(12) United States Patent
Hirose et al.

(10) Patent No.: US 7,763,737 B2
(45) Date of Patent: Jul. 27, 2010

(54) CARBAZOLE COMPOUND, AND POLYMER THEREOF

(75) Inventors: Hidekazu Hirose, Kanagawa (JP); Koji Horiba, Kanagawa (JP); Takeshi Agata, Kanagawa (JP); Katsuhiro Sato, Kanagawa (JP); Kazuaki Sato, Yamagata (JP); Yoshihiro Ohba, Yamagata (JP)

(73) Assignee: Fuji Xerox Co., Ltd., Tokyo (JP)

( * ) Notice: Subject to any disclaimer, the term of this patent is extended or adjusted under 35 U.S.C. 154(b) by 332 days.

(21) Appl. No.: 12/041,174

(22) Filed: Mar. 3, 2008

(65) Prior Publication Data

US 2008/0312453 A1 Dec. 18, 2008

(30) Foreign Application Priority Data

Jun. 15, 2007 (JP) ............................. 2007-159174

(51) Int. Cl.
*C07D 209/88* (2006.01)
(52) U.S. Cl. ....................................... 548/442; 548/444
(58) Field of Classification Search ................. 548/444, 548/442
See application file for complete search history.

(56) References Cited

U.S. PATENT DOCUMENTS

| 4,092,162 | A | 5/1978 | Wright et al. |
| 4,801,517 | A | 1/1989 | Frechet et al. |
| 4,806,443 | A | 2/1989 | Yanus et al. |
| 4,806,444 | A | 2/1989 | Yanus et al. |
| 4,937,165 | A | 6/1990 | Ong et al. |
| 4,959,288 | A | 9/1990 | Ong et al. |
| 4,983,482 | A | 1/1991 | Ong et al. |
| 5,034,296 | A | 7/1991 | Ong et al. |

| 6,652,995 | B2 * | 11/2003 | Seki et al. .................... 428/690 |
| 7,060,783 | B2 * | 6/2006 | Seki et al. .................... 528/335 |

FOREIGN PATENT DOCUMENTS

JP B2 59-28903 7/1984

(Continued)

OTHER PUBLICATIONS

Gustafsson, G. et al., "Flexible Light-emitting Diodes Made from Soluble Conducting Polymers," Letters to Nature, vol. 357 p. 477 (1992).

(Continued)

*Primary Examiner*—Kamal A Saeed
*Assistant Examiner*—Valerie Rodriguez-Garcia
(74) *Attorney, Agent, or Firm*—Oliff & Berridge, PLC

(57) ABSTRACT

The present invention provides a carbazole compound represented by the following formula (I):

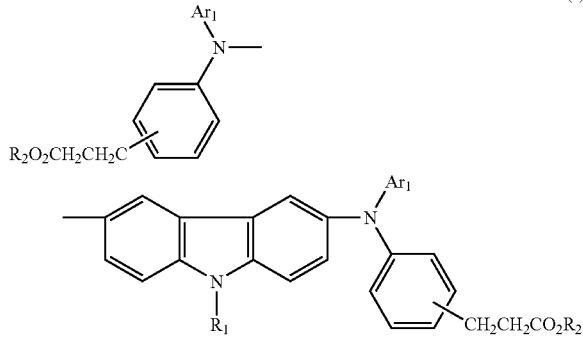

wherein each $Ar_1$ independently represents a substituted or unsubstituted monovalent aromatic group or an aromatic group containing a heteroring, and $R_1$ and each $R_2$ independently represent a hydrogen atom, an alkyl group, a substituted or unsubstituted aryl group, or a substituted or unsubstituted aralkyl group.

2 Claims, 10 Drawing Sheets

FOREIGN PATENT DOCUMENTS

| | | |
|---|---|---|
| JP | A 61-20953 | 1/1986 |
| JP | A 01-134456 | 5/1989 |
| JP | A 01-134457 | 5/1989 |
| JP | A 01-134462 | 5/1989 |
| JP | A 04-133065 | 5/1992 |
| JP | A 04-133066 | 5/1992 |
| JP | A 2001-244077 | 9/2001 |
| JP | A 2001-257076 | 9/2001 |

OTHER PUBLICATIONS

Sugihare, M. et al., "Synthesis and Physical Properties of Polyphosphazenes Having Hole-Transporting Aromatic Tertiary Amines in Side Chains," Polymer Preprints, Japan vol. 42, No. 7 20J-21 (1993).

\* cited by examiner

CARBAZOLE COMPOUND, AND POLYMER THEREOF

CROSS-REFERENCE TO RELATED APPLICATIONS

This application is based on and claims priority under 35 USC 119 from Japanese Patent Application No. 2007-159174 filed on Jun. 15, 2007.

BACKGROUND

1. Technical Field

The present invention relates to a novel carbazole compound, and a polymer thereof.

2. Related Art

As charge transporting materials, charge transporting polymers, a typical example of which is polyvinylcarbazole (PVK), and low molecular weight compound dispersed systems, wherein a charge transporting low molecular weight compound is dispersed in a polymer, are well-known. In organic electrophotographic photoreceptors used in recent copying machines or printers, the low molecular weight compound dispersed systems are mainly used since the use of various materials is permissible and high functionality is possible due to a combination of a low molecular weight compound and a polymer, or the like. The charge transporting polymers have also been investigated as photoconductive materials or charge transporting materials for electrophotographic photoreceptors since they may provide high functionality and a long lifetime. In recent years, the polymers are also used as organic electroluminescent element materials.

SUMMARY

According to an aspect of the present invention, there is provided a carbazole compound represented by the following formula (I):

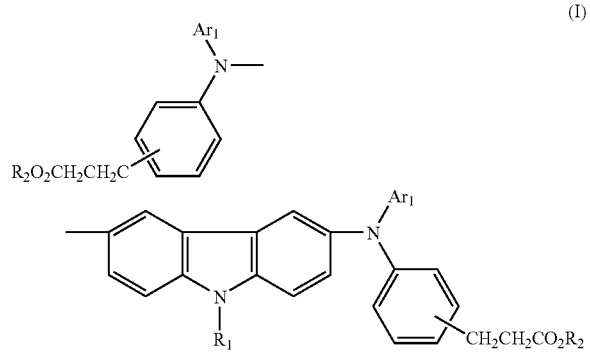

wherein each $Ar_1$ independently represents a substituted or unsubstituted monovalent aromatic group or aromatic group containing a heteroring, and $R_1$ and each $R_2$ independently represent a hydrogen atom, an alkyl group, a substituted or unsubstituted aryl group, or a substituted or unsubstituted aralkyl group.

BRIEF DESCRIPTION OF THE DRAWINGS

Exemplary embodiments of the present invention will be described in detail based on the following figures, wherein.

DETAILED DESCRIPTION

Figure 1:
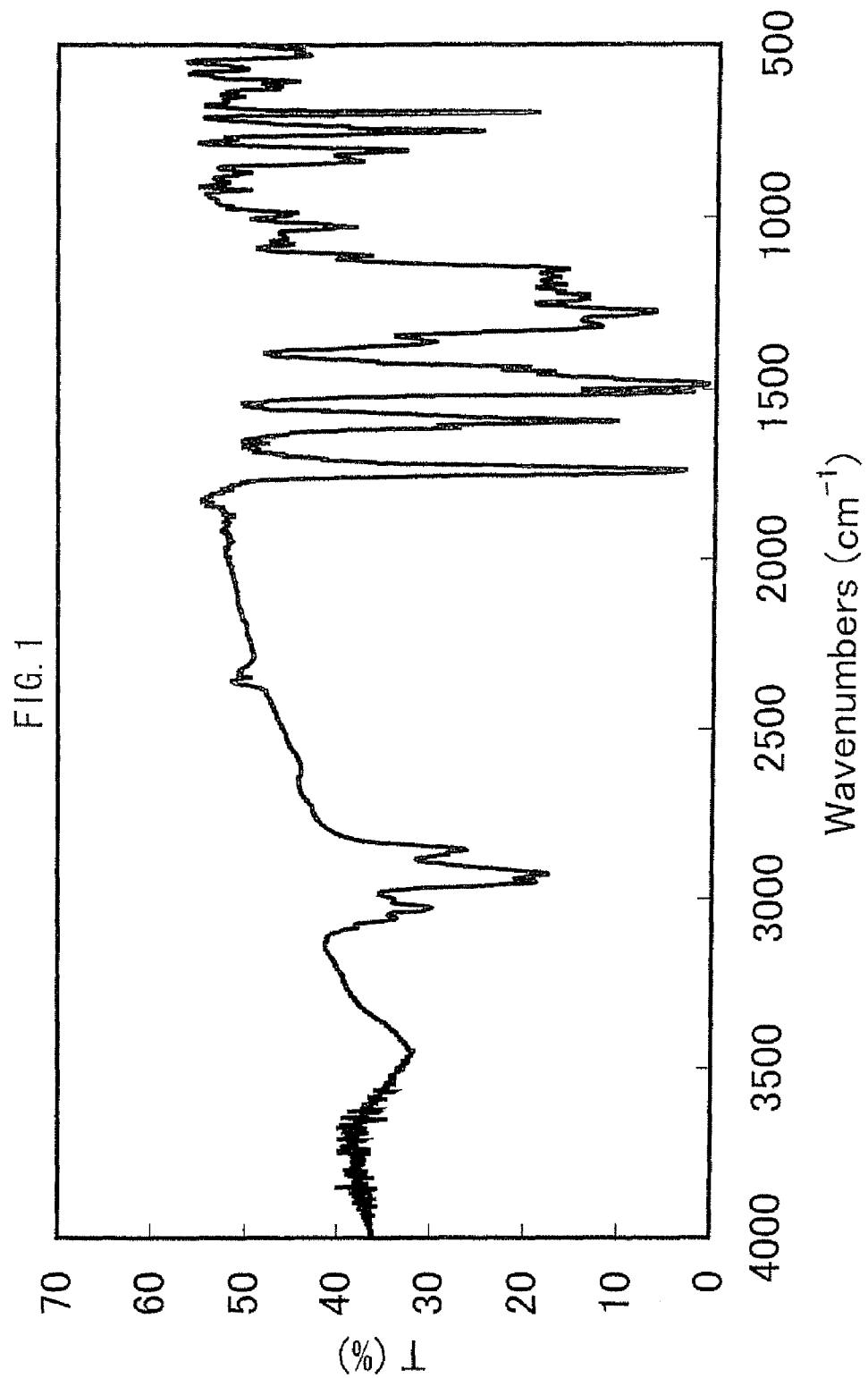
FIG. 1 is an IR spectrum of a compound obtained in Example 1.

The carbazole compound of the present exemplary embodiment is a carbazole compound represented by the following formula (I):

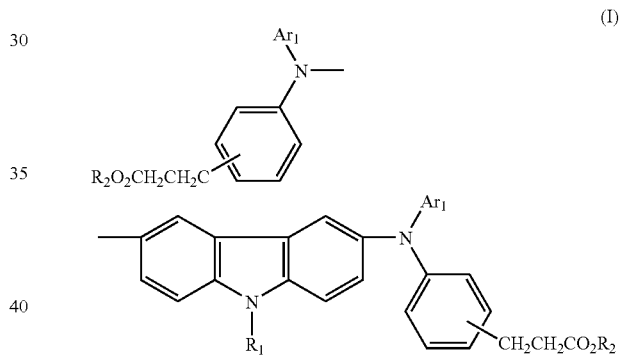

In the formula (I), each $Ar_1$ independently represents a substituted or unsubstituted monovalent aromatic group or aromatic group containing a heteroring, and $R_1$ and each $R_2$ independently represent a hydrogen atom, an alkyl group, a substituted or unsubstituted aryl group, or a substituted or unsubstituted aralkyl group.

The carbazole compound polymer of the present exemplary embodiment is a carbazole compound polymer represented by the following formula (II):

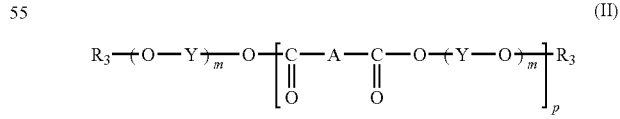

In the formula (II), each Y independently represents a bivalent hydrocarbon group, each $R_3$ independently represents a hydrogen atom, an alkyl group, a substituted or unsubstituted aryl group, or a substituted or unsubstituted aralkyl group, each m independently represents an integer of from 1 to 5, p represents an integer of from 5 to 5,000, and A represents a group represented by the following formula (III):

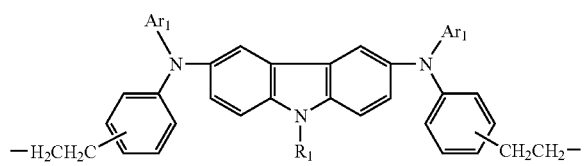
(III)

In the formula (III), each Ar₁ independently represents a substituted or unsubstituted monovalent aromatic group or aromatic group containing a heteroring, and $R_1$ represents a hydrogen atom, an alkyl group, a substituted or unsubstituted aryl group, or a substituted or unsubstituted aralkyl group.

As described above, each $Ar_1$ in the formulae (I) and (III) independently represents a substituted or unsubstituted monovalent aromatic group or aromatic group containing a heteroring, and the number of the aromatic ring(s) and that of the heteroring(s) are not particularly limited.

Specifically, each $Ar_1$ independently represents a substituted or unsubstituted phenyl group, a substituted or unsubstituted monovalent polynuclear aromatic hydrocarbon group having an aromatic number of from 2 to 20, a substituted or unsubstituted monovalent condensed aromatic hydrocarbon group having an aromatic number of from 2 to 20, a substituted or unsubstituted monovalent aromatic heterocyclic group, or a substituted or unsubstituted monovalent aromatic group having at least one aromatic heteroring.

In the invention, the "polynuclear aromatic hydrocarbon" specifically means a polycyclic aromatic hydrocarbon defined below. Moreover, in the invention, the "condensed aromatic hydrocarbon" specifically means a polycyclic aromatic hydrocarbon defined below.

The "polynuclear aromatic hydrocarbon" means a hydrocarbon wherein 2 or more aromatic rings composed of carbon and hydrogen are present and the rings are bonded to each other through a carbon-carbon bond. Specific examples thereof include biphenyl, terphenyl, and stilbene.

The "condensed aromatic hydrocarbon" means a hydrocarbon wherein 2 or more aromatic rings composed of carbon and hydrogen are present and the aromatic rings share a pair of adjacent carbon atoms that are bonded to each other. Specific examples thereof include naphthalene, anthracene, phenanthrene, pyrene, perylene, and fluorene.

In the formulae (I) and (III), the "aromatic heteroring" selected as one of the structures which each $Ar_1$ may represent means an aromatic ring which may also contain one or more elements other than carbon and hydrogen. The number (Nr) of the atoms which constitute the cyclic skeleton thereof is desirably either one of five or six, or both thereof.

The kind and the number of the atom(s) (i.e., the heteroatoms) which (partially) constitute(s) the cyclic skeleton and is/are other than carbon atoms are not limited. The heteroatom(s) is/are desirably, for example, one or more sulfur atoms, one or more nitrogen atoms and/or one or more oxygen atoms. The cyclic skeleton may contain two or more kinds of heteroatoms, and/or two or more heteroatoms.

It is particularly desired to use, as a heteroring having a 5-membered ring structure, thiophene, pyrrole or furan, or a heteroring wherein the carbon atoms at the 3- and 4-positions thereof are further substituted with nitrogen atoms.

It is desired to use, as a heteroring having a 6-membered ring, a pyridine ring.

The aromatic group containing an aromatic heteroring, which is selected as one of the structures which each $Ar_1$ may represent in the formulae (I) and (III), means an aromatic group which may contain, in the atomic group which constitutes its skeleton, at least one aromatic heteroring, this aromatic heteroring being as defined above. This may be an aromatic group the whole of which is made of a conjugated system, or an aromatic group a part of which is made of a conjugated system. From the viewpoint of charge transporting performance, the former is desired.

In the formulae (I) and (III), examples of the substituent of the monovalent aromatic group represented by each $Ar_1$ include hydrogen and halogen atoms, and alkyl, alkoxy, phenoxy, aryl, aralkyl, and substituted amino groups.

The alkyl group is desirably a group having 1 to 10 carbon atoms, and examples thereof include methyl, ethyl, propyl and isopropyl groups.

The alkoxy group is desirably a group having 1 to 10 carbon atoms, and examples thereof include methoxy, ethoxy, propoxy, and isopropoxy groups.

The aryl group is desirably a group having 6 to 20 carbon atoms, and examples thereof include phenyl, and toluyl groups.

The aralkyl group is desirably a group having 7 to 20 carbon atoms, and examples thereof include benzyl, and phenethyl groups.

The substituent of the substituted amino group may be an alkyl, aryl, or aralkyl group, and specific examples thereof are as described above.

As described, $R_1$ in the formulae (I) and (III) represents a hydrogen atom, an alkyl group, a substituted or unsubstituted aryl group, or a substituted or unsubstituted aralkyl group.

The alkyl group is desirably a group having 1 to 10 carbon atoms, and examples thereof include methyl, ethyl, propyl and isopropyl groups.

The aryl group is desirably a group having 6 to 20 carbon atoms, and examples thereof include phenyl, and toluyl groups.

The aralkyl group is desirably a group having 7 to 20 carbon atoms, and examples thereof include benzyl, and phenethyl groups.

The substituent in the substituted aryl or aralkyl group may be, for example, an alkyl, aryl, or aralkyl group, and specific examples thereof are as described above.

Each of $R_2$s in the formula (I) is identical to $R_1$ in the formulae (I) and (III).

Ys in the formula (II) each represent a group selected from the following structural formulae (IV-1) to (IV-7):

(IV-1)

(IV-2)

(IV-3)

(IV-4)

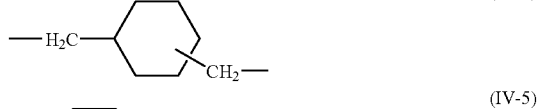
(IV-5)

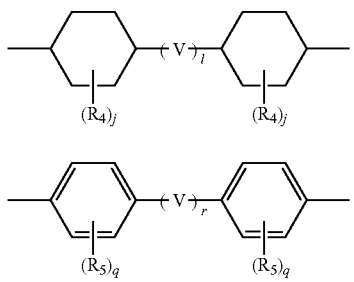

In the above-mentioned structural formulae, $R_4$(s) and $R_5$(s) each represent a hydrogen atom, an alkyl group having 1 to 4 carbon atoms, an alkoxy group having 1 to 4 carbon atoms, a substituted or unsubstituted phenyl group, or a substituted or unsubstituted aralkyl group; h and i each independently represent an integer of 1 to 5; l and r each independently represent 0 or 1; j and q each independently represent 0, 1 or 2; and v represents a group selected from groups represented by structural formulae (V-1) to (V-11) illustrated below.

The aralkyl group which each of $R_4$ and $R_5$ in the above-mentioned structural formulae represents, and the substituent in the substituted phenyl and the substituted aralkyl group therein are identical to the aralkyl group which $R_1$ in the formulae (I) and (III) represents, and the substituent in the substituted phenyl and the substituted aralkyl groups therein, respectively.

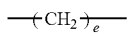 (V-1)

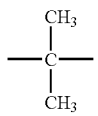 (V-2)

 (V-3)

 (V-4)

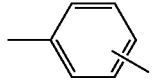 (V-5)

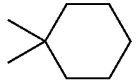 (V-6)

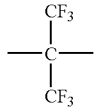 (V-7)

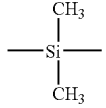 (V-8)

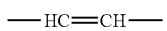 (V-9)

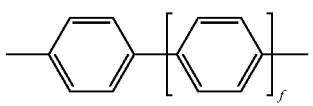 (V-10)

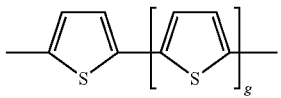 (V-11)

In the structural formulae (V-1), (V-10) and (V-11), e represents an integer of 1 to 5, and f and g each represent an integer of 0 to 5.

Each $R_3$ in the formula (II) is identical to $R_1$ in the formulae (I) and (III).

The polymerization degree of the polymer of the present exemplary embodiment represented by the formula (II) is from 5 to 5,000. The polymerization degree is desirably from 10 to 1,000 because of the film-formability, the stability of the electric device element, wherein the polymer is to be used, and others. The weight-average molecular weight Mw is desirably from 10,000 to 300,000.

In the carbazole compound represented by the formula (I), each $Ar_1$, $R_1$ and $R_2$ is desirably in a combination selected from the following:

each $Ar_1$ is independently a phenyl, naphthyl, biphenyl, terphenyl or phenylthiophene group, $R_1$ is a methyl, ethyl, phenyl, naphthyl, or biphenyl group, and each $R_2$ is independently a methyl, ethyl, or i-propyl group.

More desirably each $Ar_1$ is independently a phenyl, naphthyl, or biphenyl group, $R_1$ is a methyl, phenyl, or biphenyl group, and each $R_2$ is independently a methyl, or ethyl group.

In the carbazole compound polymer represented by the formula (II), A, each Y, m, and $R_3$ are desirably in a combination selected from the following.

A is the above-mentioned desired structure, each Y is independently a methylene, ethylene, i-propylene, or cyclohexylene group, each m is independently from 1 to 5, and each $R_3$ is independently a methyl, ethyl, or phenyl group.

More desirably, A is the above-mentioned desired structure, each Y is independently a methylene, or ethylene group, each m is independently from 1 to 3, and each $R_3$ is independently a methyl, or ethyl group.

With respect to the carbazole compound and the polymer of the exemplary embodiment, specific examples (compound exemplifying numbers: [1] to [25]) of the carbazole compound represented by the formula (I) are shown in <List (1)>, and specific examples (polymer exemplifying numbers: [1] to [30]) of the carbazole compound polymer represented by the formula (II) are shown in <List (2)>. However, the compound and the polymer are not limited thereto. In the specific examples of <List (2)> described below, $R_3$s in the formula (II) each represent a hydrogen atom, an alkyl group, a substituted or unsubstituted aryl group, or a substituted or unsubstituted aralkyl group.

<List(1)>:
Specific examples of the carbazole compound represented by the formula (I)

| Compound exemplifying number | $Ar_1$ | $R_1$ | $R_2$ | Bonding position |
|---|---|---|---|---|
| [1] | phenyl | H | $CH_3$ | 3 |
| [2] | biphenyl-4-yl | H | $CH_3$ | 4 |
| [3] | 3,4-dimethylphenyl | H | $CH_3$ | 4 |
| [4] | phenyl | $CH_3$ | $CH_3$ | 4 |
| [5] | biphenyl-4-yl | $CH_3$ | $CH_2CH_3$ | 4 |
| [6] | phenyl | $n\text{-}C_3H_7$ | $CH_2CH_3$ | 4 |
| [7] | 4-methoxyphenyl | $n\text{-}C_3H_7$ | $CH_3$ | 4 |
| [8] | 9,9-dimethylfluoren-2-yl | $n\text{-}C_3H_7$ | $CH_3$ | 4 |
| [9] | phenyl | $C_6H_{13}$ | $CH_3$ | 4 |
| [10] | biphenyl-4-yl | $C_6H_{13}$ | $CH_2CH_3$ | 4 |
| [11] | 3,4-dimethylphenyl | $C_6H_{13}$ | $CH_3$ | 3 |
| [12] | 4-methoxyphenyl | $C_6H_{13}$ | $CH_3$ | 4 |
| [13] | 4-(thiophen-2-yl)phenyl | $C_6H_{13}$ | $CH_3$ | 4 |

-continued

<List(1)>:
Specific examples of the carbazole compound represented by the formula (I)

| Compound exemplifying number | Ar₁ | R₁ | R₂ | Bonding position |
|---|---|---|---|---|
| [14] | phenyl | phenyl | CH₃ | 4 |
| [15] | biphenyl-4-yl | phenyl | CH₃ | 4 |
| [16] | 9,9-dimethylfluoren-2-yl | phenyl | CH₃ | 4 |
| [17] | 4-(9,9-dimethylfluoren-2-yl)phenyl | phenyl | CH₃ | 4 |
| [18] | phenyl | 4-methylphenyl | CH₃ | 4 |
| [19] | 4-(thiophen-2-yl)phenyl | 4-methylphenyl | CH₂CH₃ | 4 |
| [20] | phenyl | 2,6-dimethylphenyl | CH₃ | 4 |
| [21] | biphenyl-4-yl | 2,6-dimethylphenyl | CH₂CH₃ | 4 |
| [22] | 7-(thiophen-2-yl)-9,9-dimethylfluoren-2-yl | 2,6-dimethylphenyl | CH₂CH₃ | 4 |
| [23] | 7-(5-hexylthiophen-2-yl)-9,9-dimethylfluoren-2-yl | 2,6-dimethylphenyl | CH₃ | 4 |

-continued

<List(1)>:
Specific examples of the carbazole compound represented by the formula (I)

| Compound exemplifying number | Ar$_1$ | R$_1$ | R$_2$ | Bonding position |
|---|---|---|---|---|
| [24] | H$_3$CO—⟨C$_6$H$_3$(CH$_3$)⟩—⟨C$_6$H$_4$⟩— | 2,3-(CH$_3$)$_2$C$_6$H$_3$— | CH$_3$ | 4 |
| [25] | 9-methylphenanthren-10-yl | 2,3-(CH$_3$)$_2$C$_6$H$_3$— | CH$_3$ | 4 |

<List (2)>:
Specific examples of the carbazole compound polymer represented by the formula (II)

| Polymer exemplifying number | A (Compound exemplifying number) | Ratio | Y | m |
|---|---|---|---|---|
| (1) | 4 | — | —CH$_2$CH$_2$— | 1 |
| (2) | 4 | — | 1,2-cyclohexylene | 1 |
| (3) | 4 | — | —C$_6$H$_4$—CH$_2$—C$_6$H$_4$— | 1 |
| (4) | 9 | — | —CH$_2$CH$_2$— | 1 |
| (5) | 9 | — | 3,3,5-trimethylcyclohexane-1,1-diyl(CH$_2$)(CH$_3$) | 1 |
| (6) | 10 | — | —CH$_2$CH$_2$— | 1 |
| (7) | 10 | — | 2,4-dimethylphenylene(CH$_3$) | 1 |
| (8) | 13 | — | —CH$_2$CH$_2$— | 1 |
| (9) | 13 | — | 1,4-cyclohexylene | 1 |
| (10) | 14 | — | —CH$_2$CH$_2$— | 1 |

-continued

<List (2)>:
Specific examples of the carbazole compound polymer represented by the formula (II)

| Polymer exemplifying number | A (Compound exemplifying number) | Ratio | Y | m |
|---|---|---|---|---|
| (11) | 14 | — | -C$_6$H$_4$-CH$_2$-C$_6$H$_4$- | 1 |
| (12) | 15 | — | —CH$_2$CH$_2$— | 1 |
| (13) | 15 | — | —(CH$_2$)$_6$— | 1 |
| (14) | 16 | — | —CH$_2$CH$_2$— | 1 |
| (15) | 17 | — | —CH$_2$CH$_2$— | 1 |
| (16) | 19 | — | -C$_6$H$_4$-CH$_2$-C$_6$H$_4$- | 1 |
| (17) | 19 | — | —CH$_2$CH$_2$— | 1 |
| (18) | 20 | — | —CH$_2$CH$_2$— | 1 |
| (19) | 20 | — | —(CH$_2$)$_6$— | 1 |
| (20) | 21 | — | —CH$_2$CH$_2$— | 1 |
| (21) | 21 | — | 2,4-dimethylphenyl group (with CH$_3$) | 1 |
| (22) | 22 | — | —CH$_2$CH$_2$— | 1 |
| (23) | 22 | — | —(CH$_2$)$_6$— | 1 |
| (25) | 23 | — | —CH$_2$CH$_2$— | 1 |
| (26) | 24 | — | —CH$_2$CH$_2$— | 1 |
| (29) | 9/13 | 1/1 | —CH$_2$CH$_2$— | 1 |
| (30) | 14/20 | 1/1 | —CH$_2$CH$_2$— | 1 |

[Synthesis Process]

The above-mentioned carbazole compounds and polymers may each be synthesized as follows:

(1) An arylamine and a halogenated carboalkoxyalkylbenzene, or an aryl halide and a carboalkoxyaniline are caused to react with each other to synthesize a diarylamine. Next, this diarylamine and an aryl bishalide are caused to react with each other.

(2) An arylamine or a benzidine derivative, and a halogenated carboalkoxyalkylbenzene are caused to react with each other to synthesize a diarylamine. Next, this diarylamine and an aryl halide are caused to react with each other.

As described in JP-A No. 05-80550, with respect to the synthesis of a charge transporting material having an alkylenecarboxylic acid ester, disclosed is a process of introducing a chloromethyl group, forming a Grignard's reagent by use of Mg, converting the reagent into a carboxylic acid with carbon dioxide, and then esterifying the acid.

However, according to this method, the chloromethyl group may not be introduced from the initial stage of the raw material for synthesis since the chloromethyl group is high in reactivity.

Accordingly, it is necessary to form the skeleton of a triarylamine, tetraarylbenzidine or the like, and then subject, for example, a methyl group introduced at the initial stage of the raw material for synthesis to chloromethylation. Alternatively, it is necessary to use an unsubstituted material at the stage of the raw material for synthesis, form a tetraarylbenzidine skeleton, introduce a functional group such as a formyl group by a substitution reaction onto the aromatic ring, reduce the resultant into an alcohol, and then use a halogenating reagent such as thionyl chloride to induce the alcohol into a chloromethyl group; or subject an unsubstituted material as described above to direct chloromethylation by paraformaldehyde and hydrochloric acid.

However, the charge transporting material having the skeleton of a triarylamine, tetraarylbenzidine or the like is very high in reactivity; therefore, in the method of subjecting the introduced methyl group to chloromethylation, a reaction that substitutes halogen onto the aromatic ring is easily caused. Thus, it is substantially impossible to chlorinate only the methyl group selectively.

In the method of using an unsubstituted material at the stage of the raw material for synthesis to introduce a functional group such as a formyl group and then inducing the group into a chloromethyl group, or the direct chloromethylation method, the chloromethyl group may be introduced only onto the para-position of the nitrogen atom. Accordingly, an alkylenecarboxylic acid ester group may also be introduced only onto the para-position of the nitrogen atom.

In the method of introducing a formyl group and then inducing the group into a chloromethyl group, the reaction steps are long.

Meanwhile, the method of causing an arylamine, a diarylamine or the like to react with a halogenated carboalkoxyalkylbenzene to yield a monomer is very good since the position of the substituent is variable, and the ionization potential or the like is easily controlled. Thus, the method makes it possible to control the compound. With respect to the monomer used in the synthesis in the invention, since various substituents may easily be introduced onto an arbitrary position thereof and the monomer is chemically stable, the monomer can be easily handled, whereby the above-mentioned problems are overcome.

The process for producing the carbazole compound of the invention will be specifically described hereinafter.

In the invention, specifically, a diarylamine represented by a formula (X) illustrated below may be obtained by causing, for example, a halogenated compound represented by a formula (VI) illustrated below and an acetamide compound represented by a formula (VII) illustrated below to undergo a coupling reaction in the presence of a copper catalyst, or causing an acetamide compound represented by a formula (VIII) illustrated below and a halogenated compound represented by a formula (IX) illustrated below to undergo a coupling reaction in the presence of a copper catalyst (the coupling reaction when the diarylamine is yielded may be referred to as a "first coupling reaction" hereinafter).

Next, the diarylamine represented by the formula (X) and a dihalogenated compound represented by a formula (XI) illustrated below are caused to undergo a coupling reaction in the presence of a copper catalyst, thereby yielding a carbazole compound (the coupling reaction when the carbazole compound is yielded may be referred to as a "second coupling reaction" hereinafter).

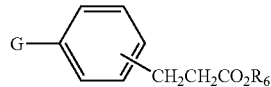
(VI)

In the formula (VI), $R_6$ represents a hydrogen atom, an alkyl group, a substituted or unsubstituted aryl group, a substituted or unsubstituted aralkyl group, and G represents a bromine or iodine atom.

Ar$_1$—NHAc (VII)

In the formula (VII), $Ar_1$ is the same as described above.

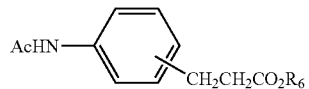
(VIII)

In the formula (VIII), $R_6$ represents a hydrogen atom, an alkyl group, a substituted or unsubstituted aryl group, a substituted or unsubstituted aralkyl group.

Ar$_1$-G (IX)

In the formula (IX), $Ar_1$ and G are the same as described above.

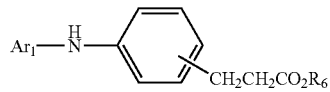
(X)

In the formula (X), $Ar_1$ and $R_6$ are the same as described above.

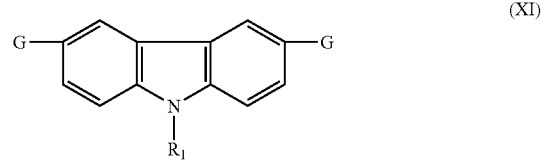
(XI)

In the formula (XI), each G and $R_1$ are the same as described above.

In the first coupling reaction, for one equivalent of an acetamide compound represented by the formula (VII) or (VIII), a halogen compound represented by the formula (VI) or (IX) is used in an amount of from 0.5 to 1.5 equivalents, desirably 0.7 to 1.2 equivalents.

The copper catalyst used in the first coupling reaction may be, for example, copper powder, cuprous oxide, or copper sulfate. The catalyst is used desirably in an amount of from 0.001 to 3 parts by mass, more desirably in an amount of from 0.01 to 2 parts by mass for 1 part by mass of the acetamide compound represented by the formula (VII) or (VIII).

In the first coupling reaction, a base may be used. For example, sodium hydroxide, potassium hydroxide, sodium carbonate, or potassium carbonate may be used. The base is used desirably in an amount of from 0.5 to 3 parts by mass, more desirably in an amount of from 0.7 to 2 parts by mass for 1 part by mass of the acetamide compound represented by the formula (VII) or (VIII).

In the first coupling reaction, a solvent may be used or may not be used.

When a solvent is used, desired examples of the solvent include water-insoluble hydrocarbon solvents having high boiling point such as n-tridecane, tetralin, p-cymene and terpinolene, and halogen-containing solvents having high boiling point such as o-dichlorobenzene and chlorobenzene. The solvent is desirably in an amount of from 0.1 to 3 parts by mass, more desirably in an amount of from 0.2 to 2 parts by mass for 1 part by mass of the acetamide compound represented by the formula (VII) or (VIII).

The first coupling reaction is conducted at 100° C. to 300° C., desirably 150° C. to 270° C., more desirably 180° C. to 230° C. under the atmosphere of an inert gas such as nitrogen or argon while the reaction solution is sufficiently effectively stirred. It is desired to conduct the reaction while removing water generated in the reaction.

After the completion of the first coupling reaction, the reaction system is optionally cooled, and then the resultant is caused to undergo hydrolysis reaction using a solvent such as methanol, ethanol, n-octanol, ethylene glycol, propylene glycol or glycerin, and a base such as sodium hydroxide or potassium hydroxide.

Specifically, after the first coupling reaction is conducted, for example, the solvent and the base are directly added to the reaction solution to conduct the hydrolysis reaction at 50° C. or higher and not higher than the boiling point of the solvent under the atmosphere of an inert gas such as nitrogen or argon while the reaction solution is sufficiently effectively stirred.

In this case, it is desired to use, as the solvent, a solvent having a high boiling point of 150° C. or higher, which permits the reaction temperature to be raised, since a carboxylic acid salt is generated and solidified in the coupling reaction. It is particularly desired to use ethylene glycol, propylene glycol, glycerin or some other water-soluble compound in post treatment after the hydrolysis reaction in order to isolate a diarylamine compound represented by the formula (X) by neutralizing the reaction solution with hydrochloric acid or the like after water is poured into the solution.

The solvent is used in an amount of from 0.5 to 10 parts by mass, desirably from 1 to 5 parts by mass for 1 part by mass of the acetamide compound represented by the formula (VII) or (VIII).

The base is used in an amount of from 0.2 to 5 parts by mass, desirably 0.3 to 3 parts by mass for 1 part by mass of the acetamide compound represented by the formula (VII) or (VIII).

After the completion of the hydrolysis reaction, the reaction product is poured into water, and further, the resultant is neutralized with hydrochloric acid or the like, thereby isolating a diarylamine compound represented by the formula (X) (post treatment). Next, the resultant is sufficiently washed, and optionally dissolved into an appropriate solvent. Thereafter, the resultant is subjected to column purification using silica gel, alumina, activated clay, activated carbon or the like, or treatment in which an adsorbent such as those mentioned above is added to the solution so as to adsorb unnecessary components thereon or the like is conducted. Furthermore, the resultant is recrystallized from an appropriate solvent such as acetone, ethanol, ethyl acetate, or toluene. Alternatively, it is allowable to subject the resultant compound to esterification such as methyl-esterification or ethyl-esterification, and then conduct the same operation.

Next, the diarylamine compound, which is represented by the formula (X) and is yielded as described above, and a halogen compound represented by formula (XI) are caused to undergo coupling reaction (second coupling reaction) in the presence of a copper catalyst. The resultant is then subjected to esterification such as methyl-esterification or ethyl-esterification. Alternatively, the diarylamine compound represented by the formula (X) is subjected to esterification such as methyl-esterification or ethyl-esterification, and then the resultant is caused to undergo coupling reaction (second coupling reaction) with a dihalogen compound represented by the formula (XI) in the presence of a copper catalyst, thereby yielding a diamine compound represented by the formula (I).

In the coupling reaction (second coupling reaction) between the diarylamine compound represented by the formula (X) and the halogen compound represented by the formula (XI), for one equivalent of the compound represented by the formula (X), a dihalogen compound represented by the formula (XI) is used, as the compound represented by the formula (XI), in an amount of from 1.5 to 5 equivalents, desirably 1.7 to 4 equivalents.

The copper catalyst used may be, for example, copper powder, cuprous oxide, or copper sulfate. The catalyst is used in an amount of from 0.001 to 3 parts by mass, desirably in an amount of from 0.01 to 2 parts by mass for 1 part by mass of the diarylamine compound represented by the formula (X).

In the second coupling reaction, a base may be used. For example, sodium hydroxide, potassium hydroxide, sodium carbonate, or potassium carbonate may be used. The base is used desirably in an amount of from 1 to 6 parts by mass, more desirably in an amount of from 1.4 to 4 parts by mass for 1 part by mass of the compound represented by the formula (X).

In the second coupling reaction, a solvent may be used if necessary. Desired examples of the solvent include water-insoluble hydrocarbon solvents having high boiling point such as n-tridecane, tetralin, p-cymene and terpinolene, and halogen-containing solvents having high boiling point such as o-dichlorobenzene and chlorobenzene. The solvent is in an amount of from 0.1 to 3 parts by mass, desirably in an amount of from 0.2 to 2 parts by mass for 1 part by mass of the diarylamine compound represented by the formula (X).

The second coupling reaction is conducted at from 100° C. to 300° C., desirably 150° C. to 270° C., more desirably 180° C. to 250° C. under the atmosphere of an inert gas such as nitrogen or argon while the reaction system is sufficiently effectively stirred. It is desired to conduct the reaction while removing water generated in the reaction.

After the completion of the second coupling reaction, the reaction product is dissolved into a solvent such as toluene, ISOPAR, or n-tridecane, and the solution is optionally washed with water or filtrated to remove unnecessary components. Furthermore, the resultant is subjected to column purification using silica gel, alumina, activated clay, activated carbon or the like, or the following treatment or the like is conducted: such an adsorbent is added to the solution so as to adsorb unnecessary components thereon. Furthermore, the resultant is recrystallized from an appropriate solvent such as acetone, ethanol, ethyl acetate, or toluene to make purification.

The carbazole compound of the invention represented by the formula (I) may also be synthesized by amination reaction using a palladium catalyst. Specifically, the carbazole compound represented by the formula (I) may also be synthesized by causing a diarylamine compound represented by the formula (X) and a dihalogen compound represented by the formula (XI) in the presence of a tertiary phosphine, a palladium compound and a base.

When the amination reaction is conducted, for example, the used mole number of the diarylamine compound represented by the formula (X) is desirably from 0.5 to 4.0 times, more desirably from 0.8 to 2.0 times with respect to the mol number of the dihalogen compound represented by the formula (XI).

The tertiary phosphine is not particularly limited, and examples thereof include tertiary alkylphosphines such as triphenylphosphine, tri(t-butyl)phosphine, tri(p-tolyl)phosphine, tri(m-tolyl)phosphine, triisobutylphosphine, tricyclohexylphosphine, and triisopropylphospline. Tri(t-butyl)phosphine is desired.

The used amount of the tertiary phosphine is not particularly limited. For example, the used mol number thereof is from 0.5 to 10 times, more desirably 2.0 to 8.0 times with respect to the mol number of the palladium compound.

The palladium compound is not particularly limited, and examples thereof include bivalent palladium compounds such as palladium (II) acetate, palladium (II) chloride, palladium (II) bromide, and palladium (II) trifluoroacetate; and zero-valence palladium compounds such as tris(dibenzylideneacetone)dipalladium (0), (dibenzylideneacetone)dipalladium (0), tetrakis(triphenylphosphine)palladium (0), and palladium-carbon. Particularly desired are palladium acetate and tris(dibenzylideneacetone)dipalladium (0).

The used amount of the palladium compound is not particularly limited, and the used amount in terms of palladium is desirably from 0.001 mole % to 10 mole % with respect to the compound represented by the formula (XI), more desirably from 0.01 mole % to 5.0 mole %.

The base is not particularly limited, and examples thereof include potassium carbonate, rubidium carbonate, cesium carbonate, sodium carbonate, potassium bicarbonate, sodium bicarbonate, t-butoxypotassium, t-butoxysodium, metallic sodium, metallic potassium, and potassium hydride. Rubidium carbonate and t-butoxysodium are desired.

For example, the amount of the base is from 0.5 to 4.0 times by mole ratio, more desirably from 1.0 to 2.5 times by mole ratio with respect to the compound represented by the formula (XI).

The amination reaction is desirably conducted in an inactive solvent. The solvent that may be used is any solvent that does not hinder the present reaction remarkably. Examples thereof include aromatic hydrocarbon solvents such as benzene, toluene, xylene and mesithylene; ether solvents such as diethyl ether, tetrahydrofuran and dioxane; and other solvents such as acetonitrile, dimethylformamide, and dimethylsulfoxide. Out of these solvents, desired are aromatic hydrocarbon solvents such as toluene and xylene.

The amination reaction is conducted at normal pressure under the atmosphere of an inert gas such as nitrogen or argon. The reaction may be conducted under increased pressure. The reaction temperature may be, for example, from 20° C. to 300° C., desirably from 50° C. to 180° C. The reaction time, which may be varied in accordance with the reaction conditions, be selected, for example, in the range of several minutes (5 minutes) to 20 hours (inclusive).

After the amination reaction, the reaction solution is poured into water, and the resultant solution is sufficiently stirred. When the reaction product is crystalline, the product is filtrated by suction filtration, so as to yield a crude product. When the reaction product is oily, the solution is subjected to extraction with an appropriate solvent such as ethyl acetate or toluene, so as to yield a crude product.

Thus obtained crude product is subjected to column purification using silica gel, alumina, activated clay, activated carbon or the like, or the following treatment or some other treatment is conducted: the absorbent is added to the solution, and unnecessary components are adsorbed thereon. Furthermore, when the reaction product is crystalline, the product is recrystallized from an appropriate solvent such as hexane, methanol, acetone, ethanol, ethyl acetate or toluene, so as to be purified.

The polymer of the invention represented by the formula (II) may be synthesized by polymerizing a low molecular weight compound represented by a structural formula (XIV) illustrated below by a known method described in, for example, Experimental Chemical Lecture, 4$^{th}$ ed., Vol. 28, (edited by the Chemical Society of Japan, and published by Maruzen Co., Ltd.).

alcohol represented by HO—(Y—O)m-H, wherein m and Y are the same as described above, the same rule being applied correspondingly to m and Y in the following, and a compound represented by the above-mentioned formula (XIV), which may be referred to the "monomer" hereinafter. Using an acidic catalyst, the components are polymerized.

The acidic catalyst may be an acidic catalyst that is used in ordinary esterification reaction, such as sulfuric acid, toluenesulfonic acid, or trifluoroacetic acid. The catalyst is used in an amount of from 1/10,000 to 1/10 parts by mass, desirably from 1/1,000 to 1/50 parts by mass for 1 part by mass of the monomer.

In order to remove water generated in the synthesis, it is desired to use a solvent azeotropic with water. Effective examples of the solvent include toluene, chlorobenzene, and 1-chloronaphthalene. The solvent is used in an amount of from 1 to 100 parts by mass, desirably from 2 to 50 parts by mass for 1 part by mass of the monomer.

The reaction temperature is not particularly limited. To remove water generated in the polymerization, it is desired to conduct the reaction at the boiling point of the solvent.

After the completion of the reaction, in the case of using no solvent in the reaction, the reaction product is dissolved into a solvent in which this product may be dissolved, and the resultant reaction solution is used as described below. In the case of using the solvent, the reaction solution is used as it is.

The reaction solution is added dropwise to a poor solvent in which the polymer is slightly dissolved, such as methanol, ethanol, some other alcohol, or acetone. In this way, a polymer is precipitated. The polymer is separated, and subsequently the polymer is sufficiently washed with water or an organic solvent and then dried.

If necessary, it is allowable to repeat reprecipitation treatment of dissolving the polymer into an appropriate organic solvent, and adding the solution dropwise to a poor solvent so as to precipitate the polymer. In the reprecipitation treatment, it is desired to stir the solution effectively with a mechanical stirrer or the like. The solvent in which the polymer is dissolved in the reprecipitation treatment is used in an amount of from 1 to 100 parts by mass, desirably from 2 to 50 parts by mass for 1 part by mass of the polymer. The poor solvent is used in an amount of from 1 to 1,000 parts by mass, desirably from 10 to 500 parts by mass for 1 part by mass of the polymer.

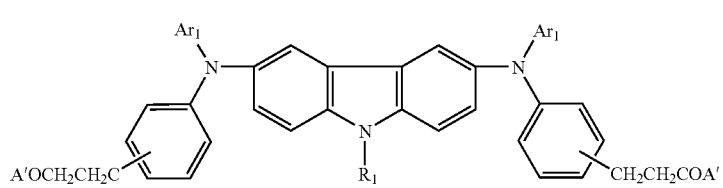

(XIV)

In the formula (XIV), each $Ar_1$ and $R_1$ are identical to $Ar_1$s and $R_1$ in the formula (I), respectively, each A' independently represents a hydroxyl group, a halogen atom, or a group —O—$R_7$, wherein $R_7$ represents an alkyl group, or a substituted or unsubstituted aryl or aralkyl group.

Specifically, the carbazole compound polymer represented by the formula (II) may be synthesized as follows:

<1> In the Case that Each A' is Independently a Hydroxyl Group:

In the case that each A' is independently a hydroxyl group, the following are mixed: equimolar amounts of a bivalent <2> In the Case that Each A' is Independently a Halogen:

In the case that each A' is independently a halogen, the following are mixed: equimolar amounts of a bivalent alcohol represented by HO—(Y—O)m-H, and a compound represented by the above-mentioned formula (XIV), which may be referred to a "monomer" hereinafter. Using an organic basic catalyst such as pyridine or triethylamine, the components are polymerized.

The organic basic catalyst is used in an amount of from 1 to 10 parts by mass, desirably from 2 to 5 parts by mass for 1 part by mass of the monomer.

Effective examples of the solvent that may be used include methylene chloride, tetrahydrofuran (THF), toluene, chlorobenzene, and 1-chloronaphthalene. The solvent is used in an amount of from 1 to 100 parts by mass, desirably from 2 to 50 parts by mass for 1 part by mass of the monomer.

The reaction temperature is not particularly limited. After the polymerization, the resultant is subjected to reprecipitation treatment as described above, so as to be purified.

In the case of using a bivalent alcohol having a high acidity, such as bisphenol, as the bivalent alcohol represented by HO—(Y—O)m-H, interfacial polymerization may be used. Specifically, water is added to the bivalent alcohol, and a base is added thereto in an amount equivalent to that of the bivalent alcohol, so as to dissolve the base to the solution. Thereafter, a solution of a monomer is added to the solution, the amount of the monomer being equivalent to that of the bivalent alcohol, while the solution is vigorously stirred, whereby polymerization can be carried out.

H. It is allowable to use a high boiling point solvent azeotropic with HO—(Y—O)m-H, such as 1-chloronaphthalene, to conduct the reaction while HO—(Y—O)m-H is removed by azeotropy under a reduced pressure.

Moreover, the carbazole compound polymer represented by the formula (II) may be synthesized as follows. In any one of the above-mentioned cases, an excessive amount of the bivalent alcohol is added to the monomer to cause the two components to react with each other, thereby producing a compound represented by a structural formula (XV) illustrated below. Thereafter, this is used as a low molecular weight compound, and caused to react with a bivalent carboxylic acid, a bivalent carboxylic halide or the like in the same way as in the above-mentioned item <2> (in the case of each A' is independently a halogen). In this way, a polymer may be obtained.

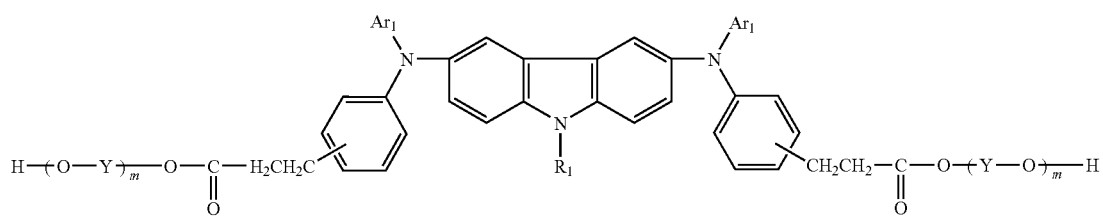

(XV)

At this time, water is used, for example, in an amount of from 1 to 1,000 parts by mass, desirably from 2 to 500 parts by mass for 1 part by mass of the bivalent alcohol.

Effective examples of the solvent in which the low molecular weight compounds are dissolved include methylene chloride, dichloroethane, trichloroethane, toluene, chlorobenzene, and 1-chloronaphthalene.

The reaction temperature is not particularly limited. In order to promote the reaction, it is desired to use a phase transfer catalyst such as an ammonium salt, or a sulfonium salt.

The phase transfer catalyst is used in an amount of from 0.1 to 10 parts by mass, desirably from 0.2 to 5 parts by mass for 1 part by mass of the monomer.

<3> In the Case that Each A' is Independently —O—$R_7$:

In the case that each A' is independently —O—$R_7$, the polymer may be synthesized by adding an excessive amount of a bivalent alcohol represented by HO—(Y—O)m-H to a monomer, and heating the system, using as a catalyst an inorganic acid such as sulfuric acid or phosphoric acid, an alkoxide titanium, an acetate salt or carbonate salt of calcium, cobalt or the like, or a zinc oxide, thereby conducting transesterification reaction.

The bivalent alcohol is used, for example, in an amount of from 2 to 100 equivalents, desirably from 3 to 50 equivalents for 1 equivalent of the monomer. The catalyst is used, for example, in an amount of from 1/1,000 to 1 part by mass, desirably from 1/100 to 1/2 parts by mass for 1 part by mass of the monomer.

The transesterification reaction is conducted at a reaction temperature of, for example, 200 to 300° C. (inclusive). After the completion of the transesterification from the group —O—$R_7$ to a group —O—(Y—O)m-H, it is desired to conduct the polymerization reaction under a reduced pressure in order to promote the reaction by leaving of HO—(Y—O)m-

In the formula (XV), each $Ar_1$, $R_1$, each Y, and each m are identical to each $Ar_1$, $R_1$, each Y, and each m in the formulae (I) and (II), respectively.

The carbazole compound and the polymer of the invention are useful for organic electronic devices such as an electrophotographic photoreceptor, an organic electroluminescent element, an organic transistor, an organic solar cell, and an organic optical memory. The compound and the polymer are excellent in charge transporting property and charge injecting property.

Charge transporting material is required to have various properties such as solubility, film-formability, charge mobility, heat resistance and charge injecting property. In order to satisfy these requirements, it is general to introduce a substituent to the material to control the physical properties thereof. Physical properties of charge transporting polymer have a high correlation with physical properties of the raw material thereof, which is a charge transporting low molecular weight compound; therefore, the molecular design of the low molecular weight compound is important. For example, the high molecular weight compound which is the raw material of a triarylamine high molecular weight compound is roughly classified into the following two:

(1) Dihydroxyarylamine (2) Bishydroxyalkylarylamine

However, the dihydroxyarylamine (1) is easily oxidized since the amine has an aminophenol structure. Thus, the amine is not easily purified. In particular, in the case of making the amine to have a p-hydroxy-substituted structure, the amine becomes more unstable. Furthermore, the amine has a structure wherein its aromatic ring is directly substituted with oxygen, so that the charge distribution thereof easily becomes an uneven distribution by the electron withdrawing property thereof. Thus, the amine has a problem that the charge mobility lowers easily.

The bishydroxyalkylarylamine (2) is not affected by the electron withdrawing property of the oxygen on the basis of the methylene group. However, it is difficult to synthesis the low molecular weight compound. Specifically, according to reaction of a diarylamine or diarylbenzidine with bromoiodobenzene, the resultant product easily becomes a mixture since both of the bromine and the iodine are reactive. As a result, the yield falls. Moreover, an alkyllithium or ethylene oxide used when the bromine is substituted with lithium is highly risky and poisonous. Thus, the amine (2) has a problem that the amine should be handled with attention.

Organic electroluminescent elements using a π conjugated polymer, a typical example of which is PPV, or a polymer wherein triphenylamine is introduced into a side chain of polyphosphazene have problems about color tone, luminescence intensity, durability, and others.

On the other hand, the carbazole compound and the carbazole compound polymer of the invention are each a compound excellent in charge transporting property, solubility and film-formability so as to have a high charge transporting property and a high luminescence property. Additionally, the carbazole compound and the carbazole compound polymer of the invention are easily synthesized, and physical properties thereof, such as the ionization potential and glass transition temperature thereof, may be controlled by introducing a substituent thereto. For this reason, the compound and the polymer are each a very useful compound as the material used in organic electronic devices such as an organic photoreceptor an organic electroluminescent element, an organic transistor, and an organic optical memory.

EXAMPLES

Hereinafter, the present invention will be described by way of the following examples; however, the invention is not limited thereto.

Example 1

Acetoanilide (25.0 g), methyl 4-iodophenylpropionate (64.4 g), potassium carbonate (38.3 g), copper sulfate pentahydride (2.3 g), and n-tridecane (50 mL) are put into a 500 mL three-necked flask, and then the solution is heated and stirred under nitrogen gas flow at 230° C. for 20 hours.

After the completion of the reaction, potassium hydroxide (15.6 g) dissolved in ethylene glycol (300 mL) is added to the solution, and then the solution is heated and refluxed under nitrogen gas flow for 3.5 hours. Thereafter, the system is cooled to room temperature, and the reaction solution is poured into 1 L of distilled water. The resultant is neutralized with hydrochloric acid to precipitate a crystal.

The crystal is collected by suction filtration, sufficiently washed with water, and transferred to a 1 L flask. Toluene (500 mL) is added thereto, and the solution is heated and refluxed. Then, water is removed by azeotropy, and then a solution wherein concentrated sulfuric acid (1.5 mL) is dissolved in methanol (300 mL) is added thereto. The resultant solution is heated and refluxed under nitrogen gas flow for 5 hours.

After the reaction, the resultant is subjected to extraction with toluene. The resultant organic layer is sufficiently washed with pure water. Next, the layer is dried with anhydrous sodium sulfate. The solvent is distilled off therefrom under a reduced pressure. The resultant is recrystallized from hexane to yield 36.5 g of DAA-1.

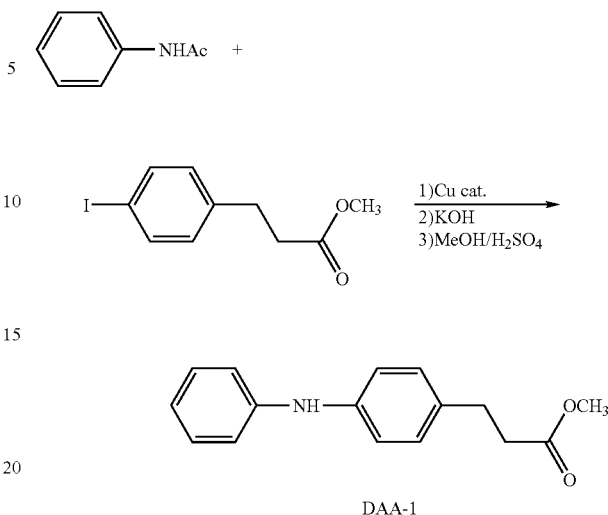

Next, a mixed solution of 9-hexylcarbazole (7.06 g), potassium iodate (2.40 g), iodine (7.72 g), and acetic acid (280 mL) is put into a 500 mL three-necked flask, and the flask is heated to 80° C. Furthermore, 20% sulfuric acid (20 mL) is added thereto, and the solution is stirred at 80° C. for 7 hours.

After the system is cooled, pure water (280 mL) is added to the solution and then powder of sodium carbonate is added thereto little by little to neutralize the solution. The resultant is subjected to extraction with toluene, and washed with a saturated aqueous solution of sodium thiosulfate, and then dried with anhydrous sodium sulfate. The solvent is distilled off therefrom, and then a crystal is precipitated from hexane and ethyl acetate. The crystal is collected by suction filtration, so as to yield 7.8 g of 3,6-diiodo-9-hexylcarbazole (a white needle crystal).

Under a nitrogen atmosphere, a mixed solution of 3,6-diiodo-9-hexylcarbazole (1.36 g), DAA-1 (1.66 g), copper (II) sulfate pentahydrate (0.135 g), potassium carbonate (1.27 g), and 1,2-dichlorobenzene is stirred at 180° C. for 30 hours. After 1,2-dichlorobenzene is distilled off, the system is cooled to room temperature, and then toluene is added to the solution. The solution is then filtrated with celite. Toluene is distilled off therefrom. The resultant product is separated by silica gel chromatography (developing solvent: hexane/ethyl acetate=4/1). In this way, 1.22 g of a compound of Compound exemplifying number [9] in <List (1)> is obtained.

Figure 2:
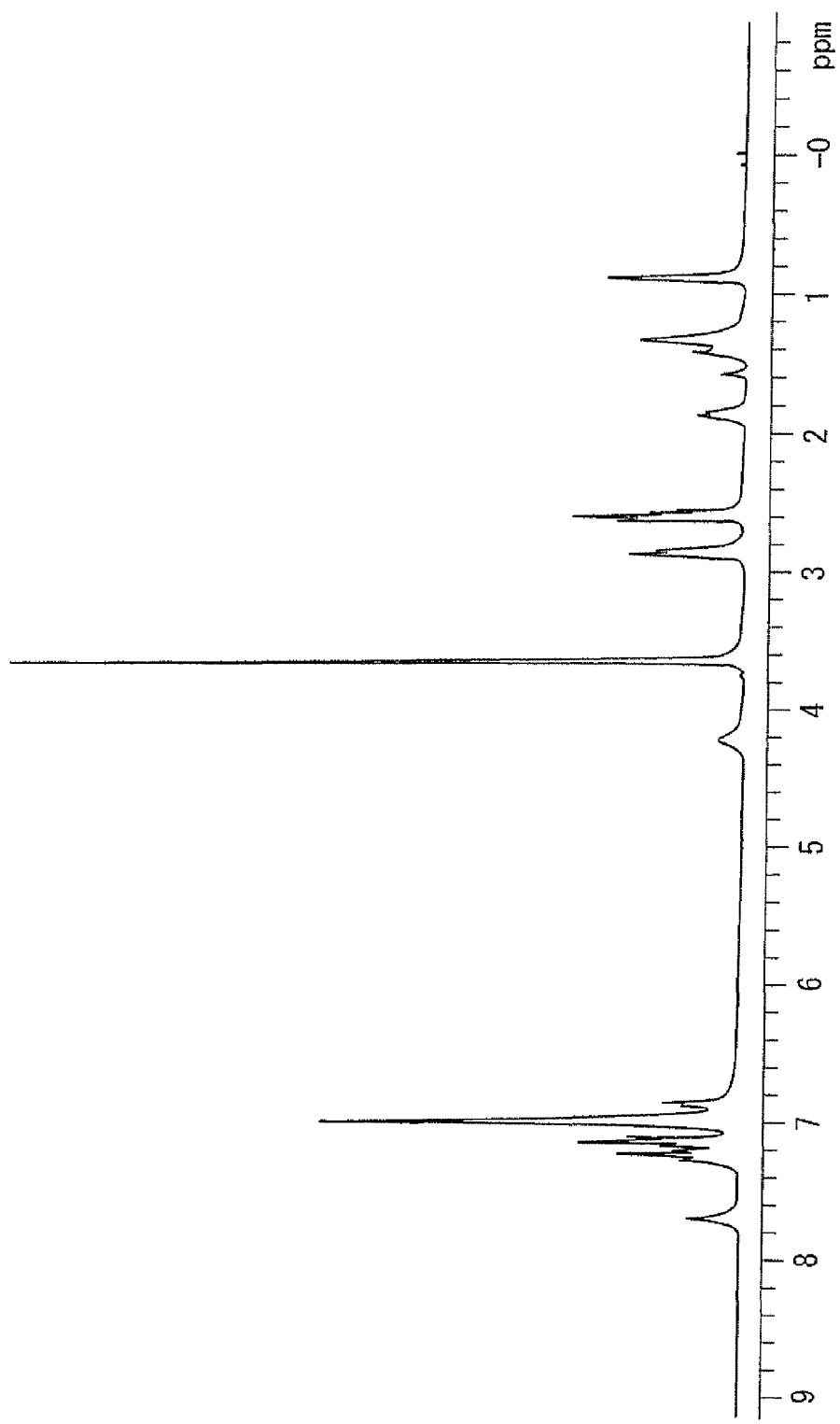
FIG. 2 is a $^1$H-NMR spectrum of the compound obtained in Example 1.

The melting point of the resultant compound of Compound exemplifying number [9] is unclear. The infrared absorption spectrum of the compound of Compound exemplifying number [9] is shown in FIG. 1, and the $^1$H NMR spectrum thereof ($^1$H-NMR, solvent: CDCl$_3$, the same being applied correspondingly to any NMR spectrum in the following) is shown in FIG. 2. In FIG. 1, the symbol "T" represents transmittance. The same is applied correspondingly to the symbol "T" in each of FIGS. 3, 5, 7 and 9.

The glass transition temperature of the compound of Compound exemplifying number [9] is 63.2° C., the ionization potential thereof is 5.31 eV, and the charge mobility thereof is $1.10 \times 10^{-7}$ cm$^2$/Vs.

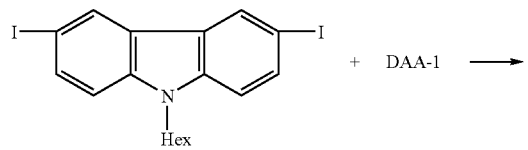

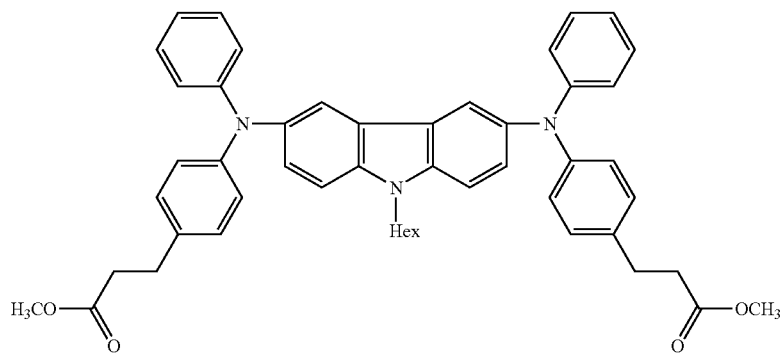

Example 2

4-(2-Thienyl)acetoanilide (30.0 g), methyl 4-iodophenylpropionate (28.5 g), potassium carbonate (13.6 g), copper sulfate pentahydride (2.0 g), and 1,2-dichlorobenzene (50 mL) are put into a 500 mL three-necked flask, and then the solution is heated and stirred under nitrogen gas flow at 230° C. for 20 hours.

After the completion of the reaction, potassium hydroxide (15.6 g) dissolved in ethylene glycol (300 mL) is added to the solution, and then the solution is heated and refluxed under nitrogen gas flow for 3.5 hours. Thereafter, the system is cooled to room temperature, and the reaction solution is poured into 1 L of distilled water. The resultant is neutralized with hydrochloric acid to precipitate a crystal.

The crystal is collected by suction filtration, sufficiently washed with water, and transferred to a 1 L flask. Toluene (500 mL) is added thereto, and the solution is heated and refluxed. Therefrom, water is removed by azeotropy, and then a solution wherein concentrated sulfuric acid (1.5 mL) is dissolved in methanol (300 mL) is added thereto. The resultant solution is heated and refluxed under nitrogen gas flow for 5 hours.

After the reaction, the resultant is subjected to extraction with toluene, and the resultant organic layer is sufficiently washed with pure water. Next, the layer is dried with anhydrous sodium sulfate, and then the solvent is distilled off therefrom under a reduced pressure. The resultant is recrystallized from hexane to yield 17.9 g of DAA-2.

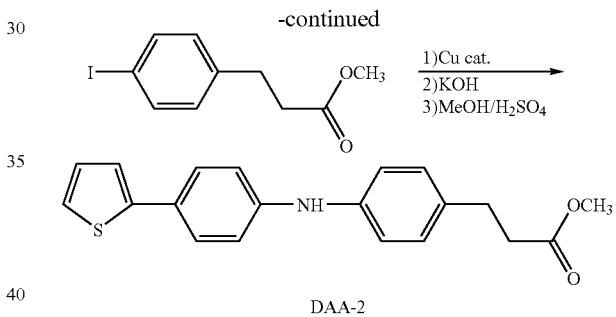

Under a atmosphere of nitrogen, a mixed solution of 3,6-diiodo-9-hexylcarbazole (1.81 g), DAA-2 (2.92 g), copper (II) sulfate pentahydrate (0.18 g), potassium carbonate (1.69 g), and 1,2-dichlorobenzene (5 mL) is stirred at 180° C. for 32 hours.

After the solution is cooled, toluene is added subsequently thereto. The solution is then filtrated with celite. Toluene is distilled off therefrom. The resultant product is separated by silica gel chromatography (developing solvent: hexane/ethyl acetate=2/1). In this way, 1.22 g of a compound of Compound exemplifying number [13] in <List (1)> is obtained.

Figure 3:
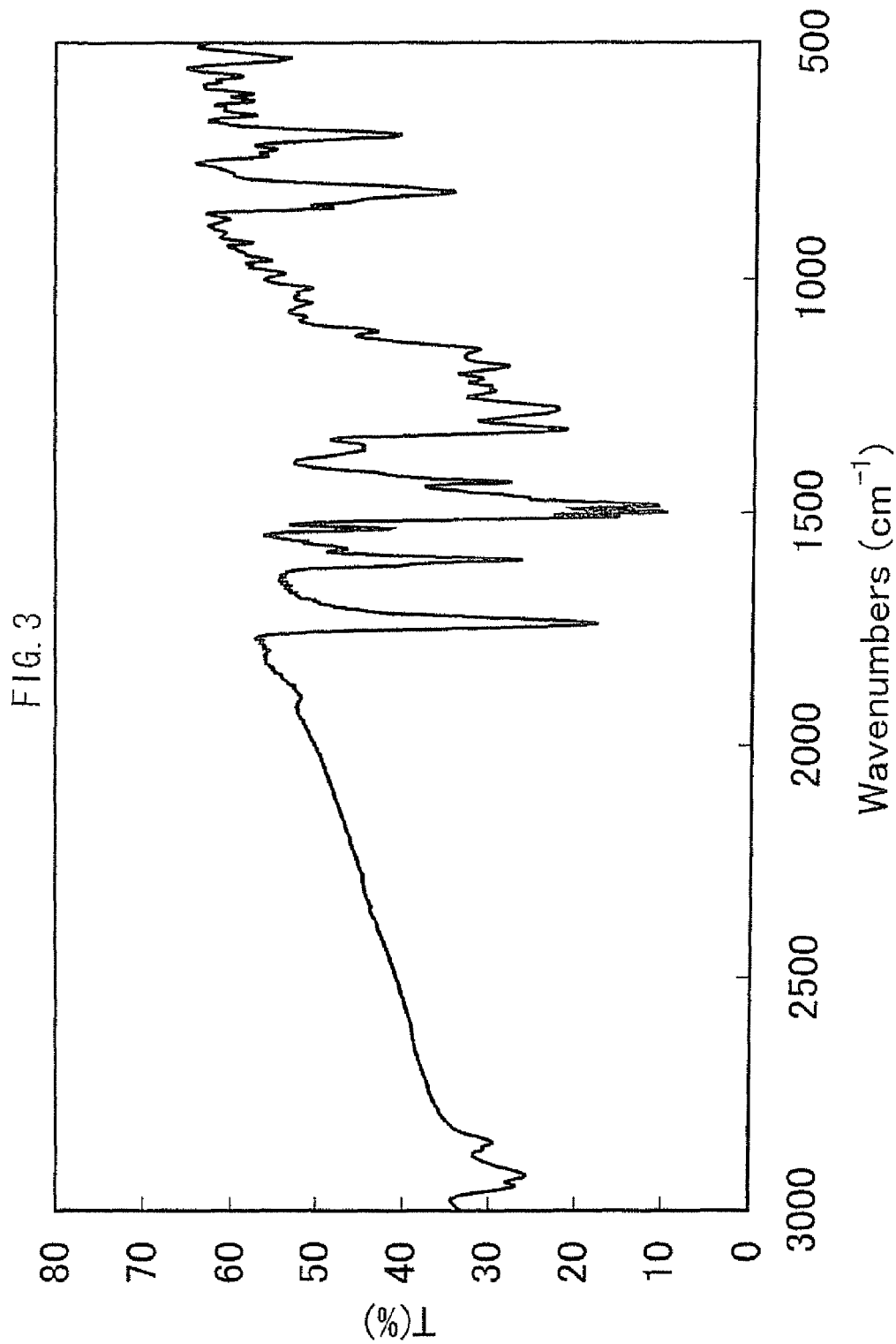
FIG. 3 is an IR spectrum of a compound obtained in Example 2.
Figure 4:
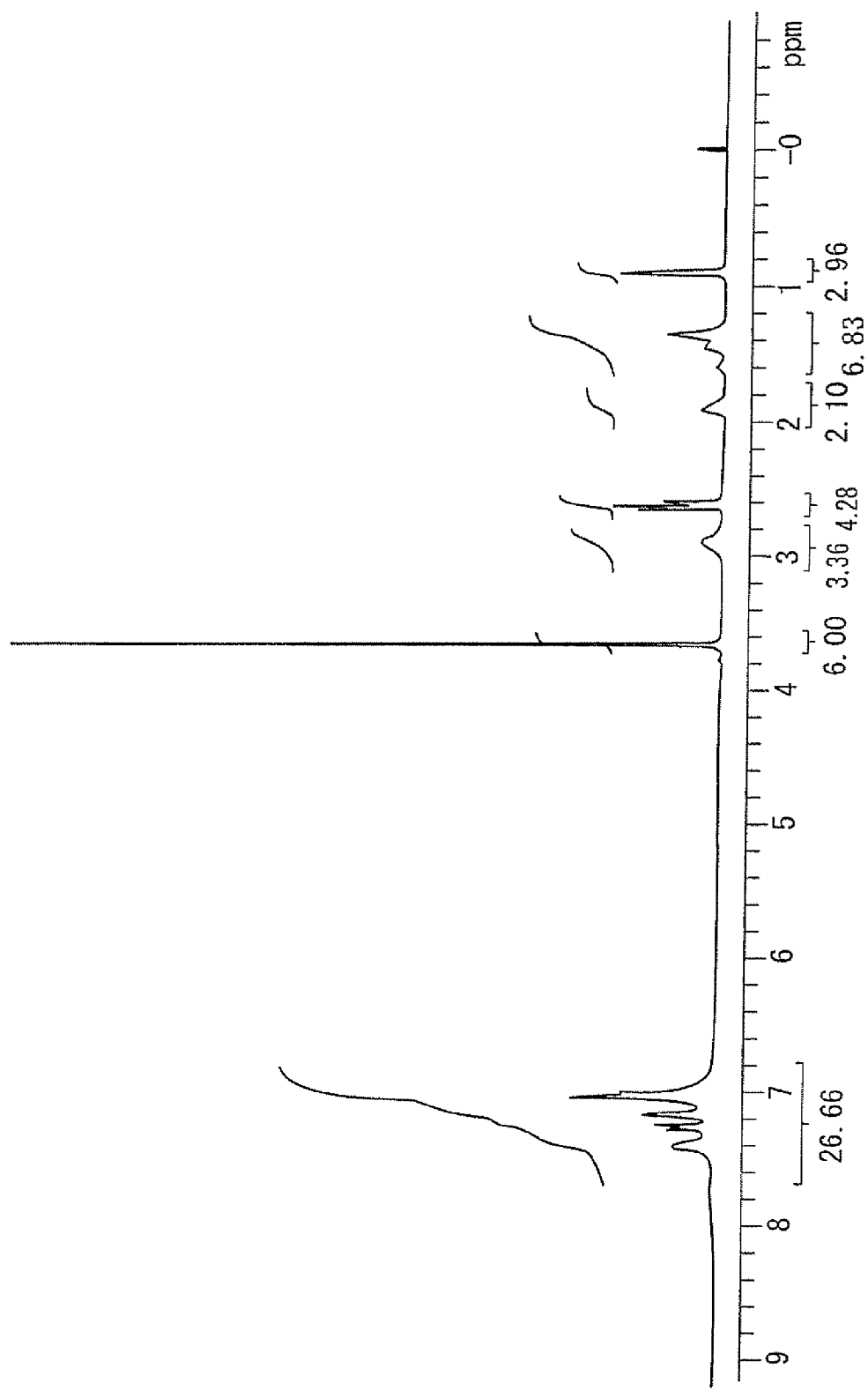
FIG. 4 is a $^1$H-NMR spectrum of the compound obtained in Example 2.

The resultant compound of Compound exemplifying number [13] is from 92 to 125° C. The infrared absorption spectrum of the compound of Compound exemplifying number [13] is shown in FIG. 3, and the $^1$H NMR spectrum thereof ($^1$H-NMR, solvent: CDCl$_3$, the same being applied correspondingly to any NMR spectrum in the following) is shown in FIG. 4.

The glass transition temperature of the compound of Compound exemplifying number [13] is 63.2° C., the ionization potential thereof is 5.32 eV, and the charge mobility thereof is $3.57 \times 10^{-7}$ cm$^2$/Vs.

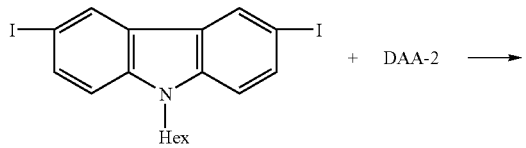

+ DAA-2 →

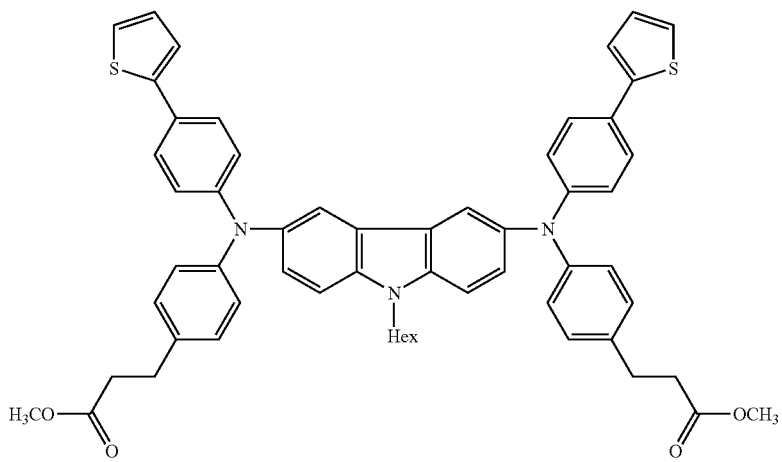

Example 3

9-Phenylcarbazole (1.22 g), potassium iodate (0.43 g), iodine (1.40 g), and acetic acid (50 mL) are put into a 100 mL three-necked flask, and the flask is heated to 80° C. Furthermore, sulfuric acid (5 mL) is added 20% thereto, and the solution is stirred at 80° C. for 8 hours.

After the system is cooled, 50 mL of pure water is added to the solution and then powder of sodium carbonate is added thereto little by little to neutralize the solution. The resultant is subjected to extraction with toluene, and washed with a saturated aqueous solution of sodium thiosulfate, and then dried with anhydrous sodium sulfate. The solvent is distilled off therefrom. The resultant white powder is recrystallized from hexane and ethyl acetate to yield 0.93 g of 3,6-diiodo-9-phenylcarbazole (a white needle crystal).

Under a atmosphere of nitrogen, 3,6-diiodo-9-phenylcarbazole (1.78 g), DAA-1 (2.20 g), copper (II) sulfate pentahydrate (0.18 g), potassium carbonate (1.69 g), and 1,2-dichlorobenzene (4 mL) are stirred at 180° C. for 15 hours. After the system is cooled, toluene is added to the solution. The solution is then filtrated with celite. Toluene is distilled off therefrom. The resultant product is separated by silica gel chromatography (developing solvent: hexane/ethyl acetate=2/1). In this way, 1.52 g of a compound of Compound exemplifying number [14] in <List (1)> is obtained (melting point: 96 to 145° C.).

Figure 5:
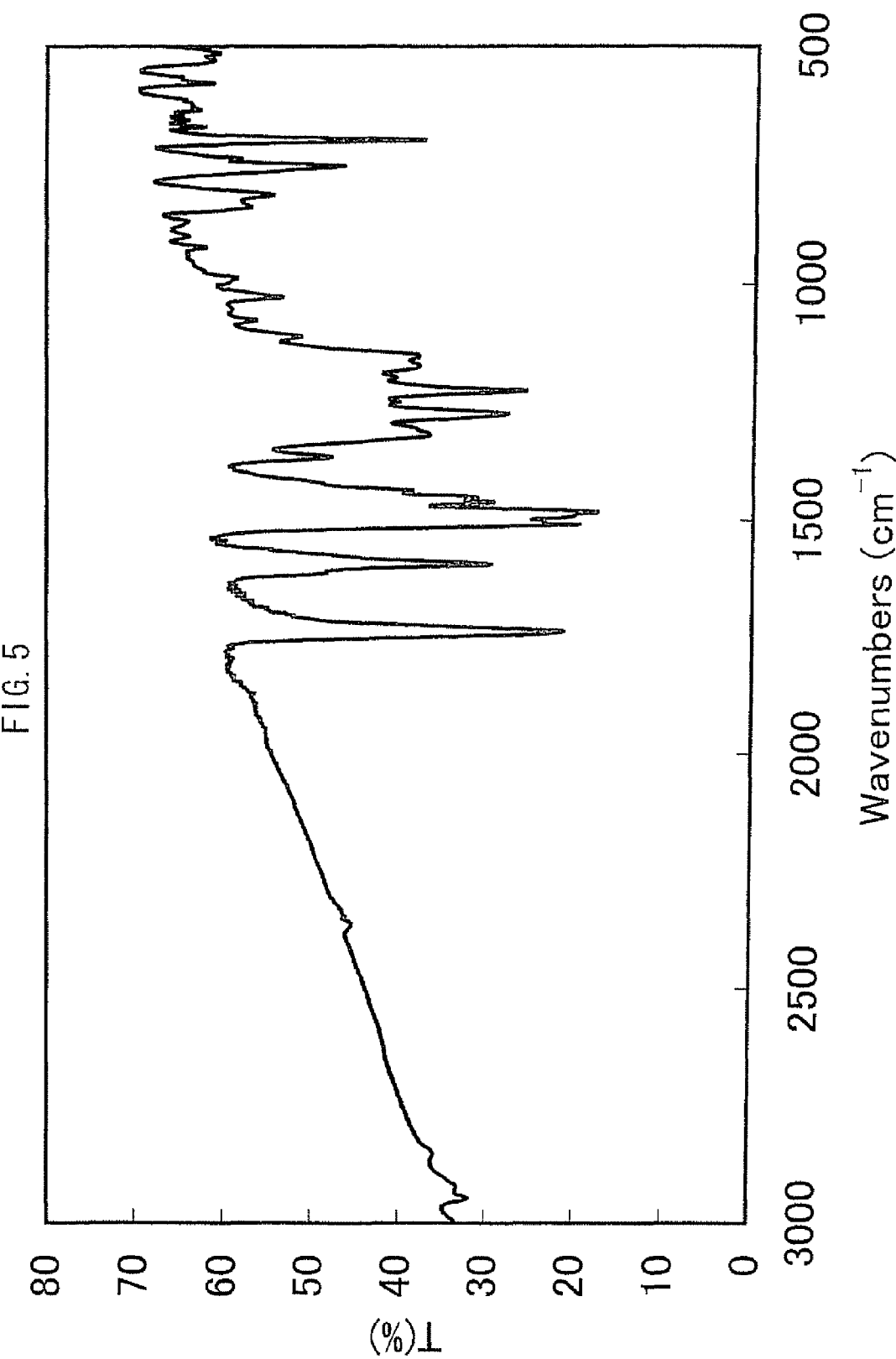
FIG. 5 is an IR spectrum of a compound obtained in Example 3.
Figure 6:
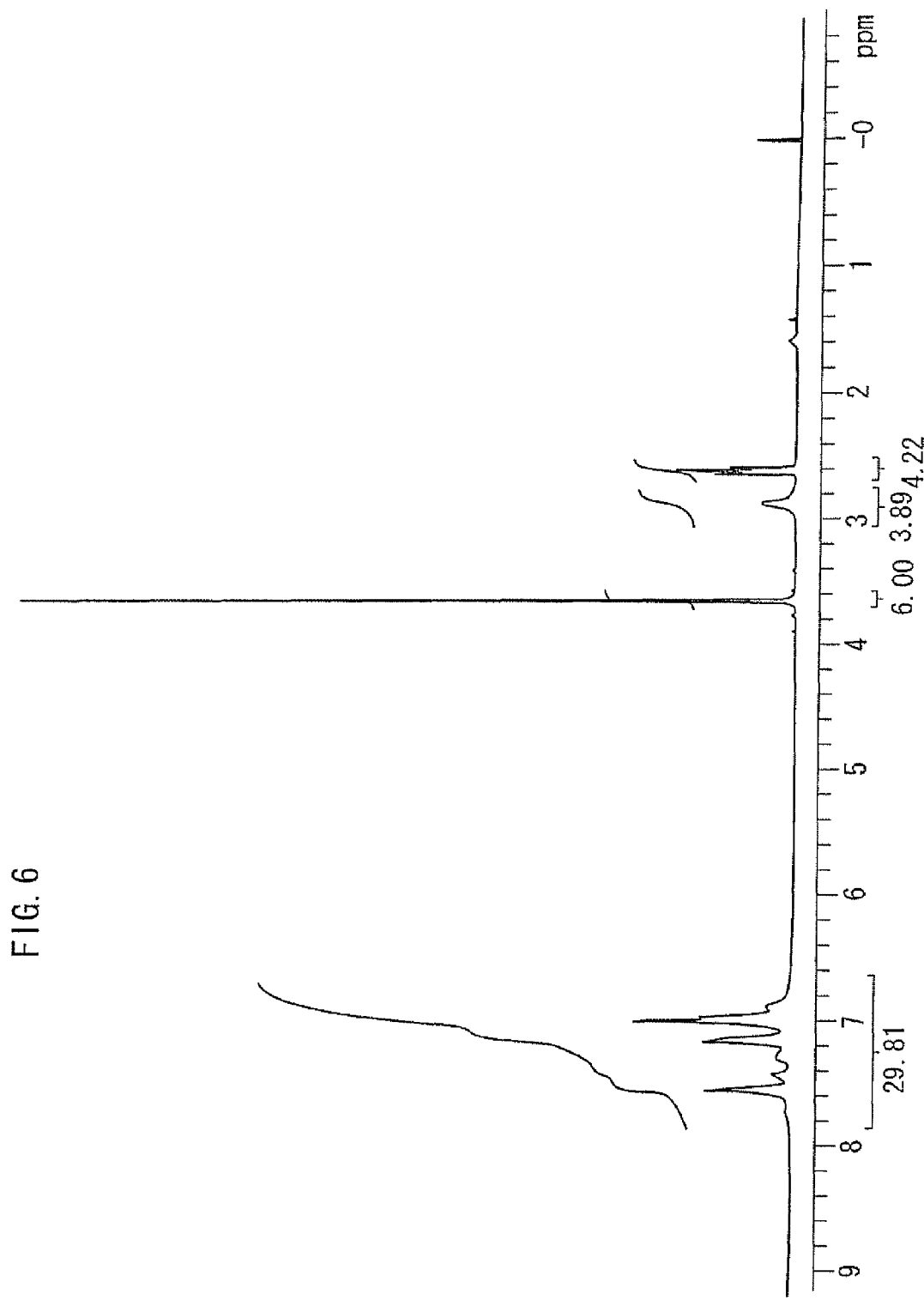
FIG. 6 is a $^1$H-NMR spectrum of the compound obtained in Example 3.

The infrared absorption spectrum of the resultant compound of Compound exemplifying number [14] is shown in FIG. 5, and the $^1$H NMR spectrum thereof ($^1$H-NMR, solvent: $CDCl_3$, the same being applied correspondingly to any NMR spectrum in the following) is shown in FIG. 6.

The glass transition temperature of the resultant compound of Compound exemplifying number [14] is 61.8° C., the ionization potential thereof is 5.42 eV, and the charge mobility thereof is $1.13 \times 10^{-7}$ $cm^2$/Vs.

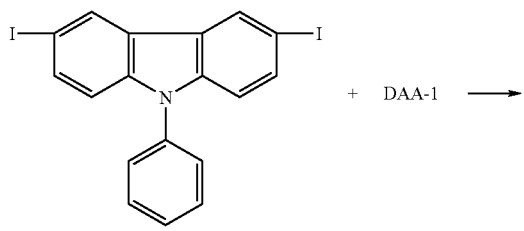

+ DAA-1 →

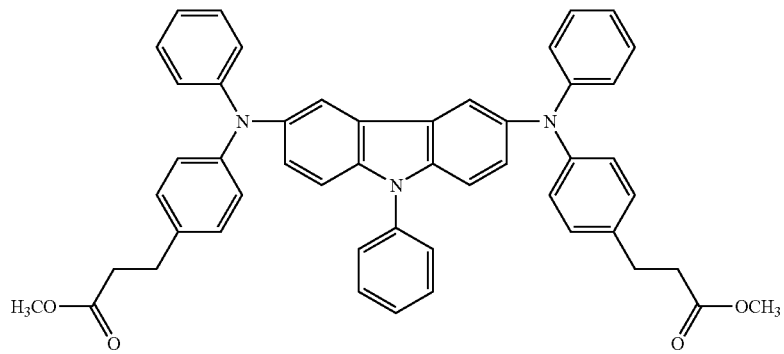

Example 4

2,2'-Dibromobiphenyl (15.6 g), bis(dibenzylideneacetone) palladium (860 mg), sodium t-butoxide (11.5 g), and toluene (200 mL) are put into a three-necked flask, and the solution is heated under the atmosphere of nitrogen. Next, tris-tert-butylphosphine (2.0 g) is added thereto. 2,6-dimethylaniline dissolved in toluene is added dropwise to the solution over about one hour while the solution is refluxed. The solution is refluxed for 2 hours, and then cooled. Thereafter, the solution is subjected to suction filtration.

200 mL of pure water is added to the filtrate, and the organic layer is extracted. The layer is washed with 100 mL of 1 N hydrochloric acid, and then anhydrous sodium sulfate is added thereto. The resultant is purified with a silica column (hexane/ethyl acetate=10/1), and then recrystallized from 100 mL of methanol to yield 10.9 g of 9-(2,6-dimethylphenyl) carbazole.

9-(2,6-Dimethylphenyl)carbazole (9.5 g), and acetic acid (350 mL) are charged into a 500 mL four-necked flask, and bromine (8.5 g) dissolved in acetic acid (50 mL) is added dropwise thereto over 30 minutes. Thereafter, the solution is stirred for 1 hour. 500 mL of pure water is added thereto, and the solution is stirred for 30 minutes. Thereafter, the solution is subjected to suction filtration to yield 13.0 g, of 3,6-dibromo-9-(2,6-dimethylphenyl)carbazole.

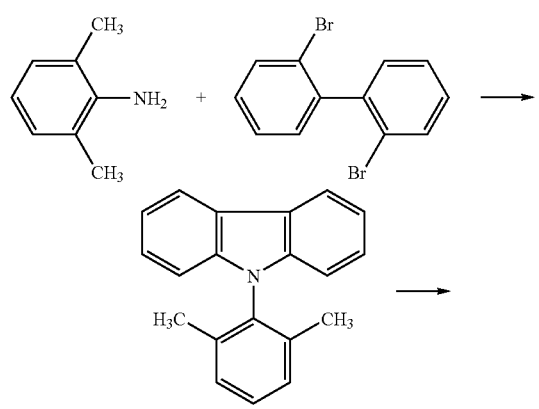

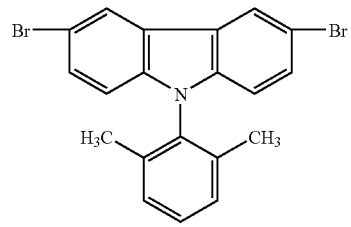

Under the atmosphere of nitrogen, a mixed solution of 3,6-dibromo-9-(2,6-dimethylphenyl)carbazole (2.15 g), DAA-1 (2.55 g), palladium acetate (0.056 g), tri-t-butylphosphine (0.152 g), and xylene (50 mL) is refluxed for 6 hours.

Figure 7:
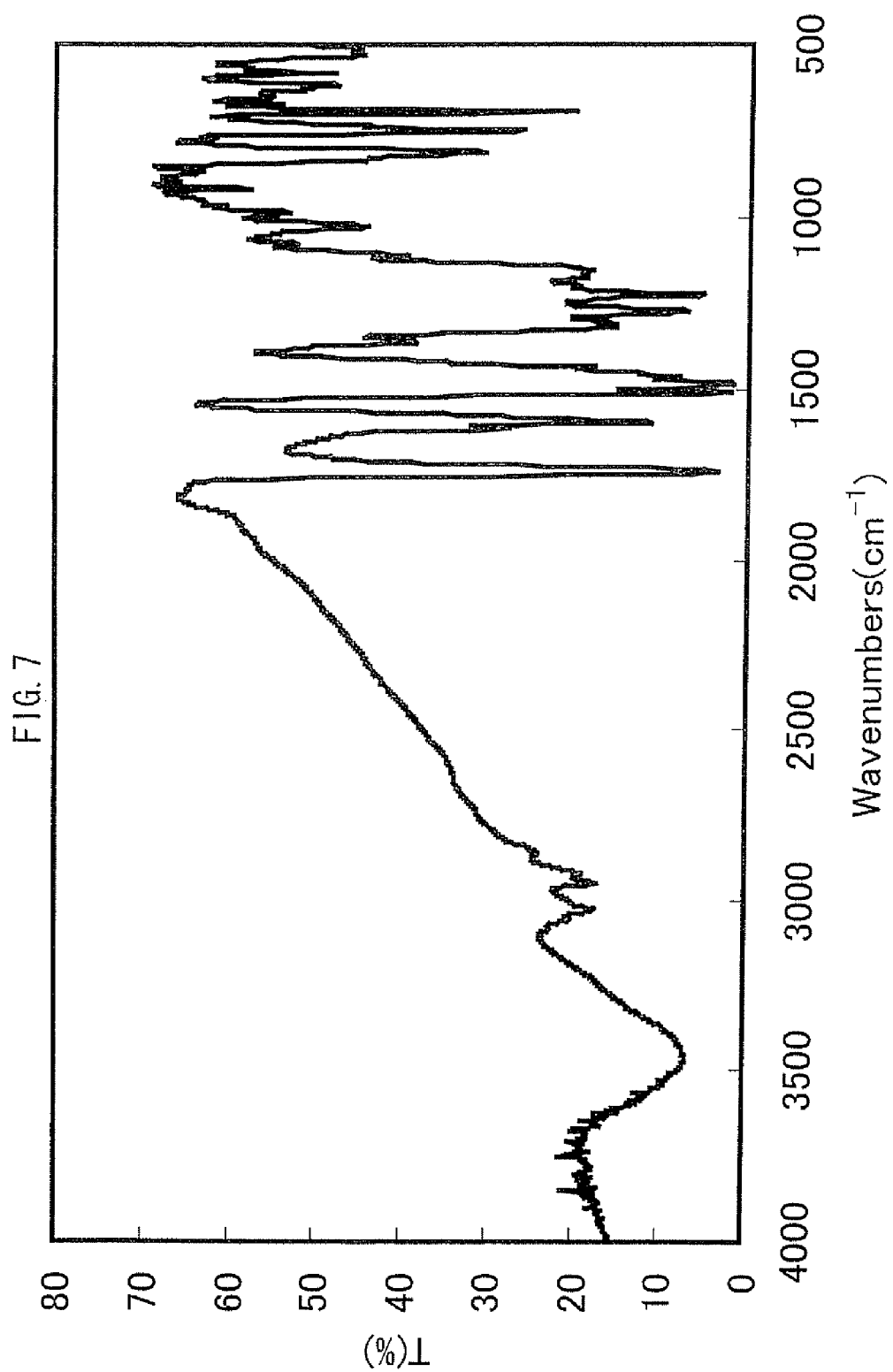
FIG. 7 is an IR spectrum of a compound obtained in Example 4.
Figure 8:
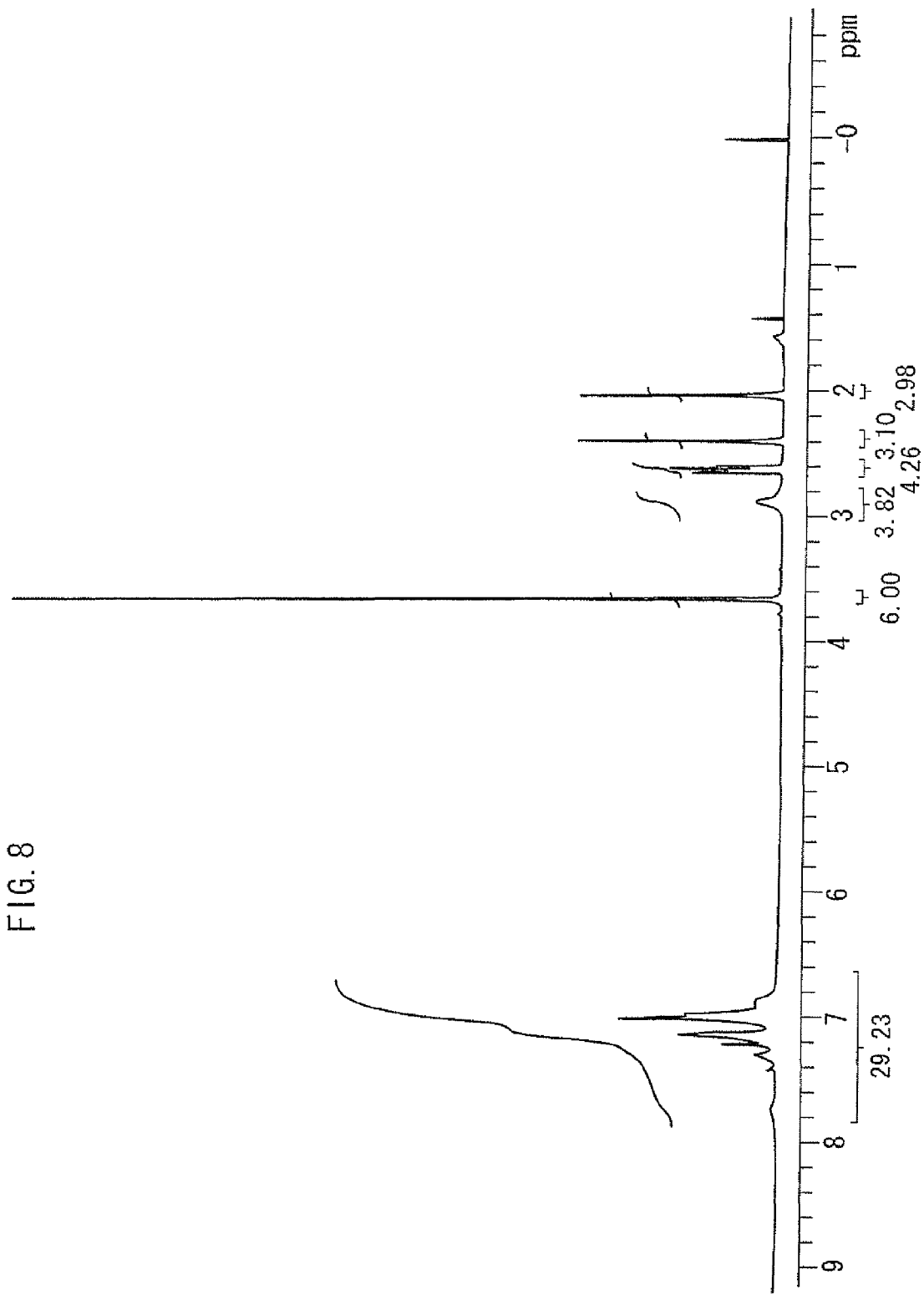
FIG. 8 is a $^1$H-NMR spectrum of the compound obtained in Example 4.

Xylene is distilled off, and then the solution is cooled to room temperature. Toluene is added thereto, and then the solution is filtrated with celite. Toluene is then distilled off therefrom. The resultant is cooled, and subjected to suction filtration, and washed with 1 N hydrochloric acid. Thereafter, the organic layer is separated, and the solvent therein is distilled off. The resultant product is separated by silica gel chromatography (developing solvent: hexane/ethyl acetate=3/1). In this way, 2.0 g of a compound of Compound exemplifying number [20] in <List (1)> is obtained. The melting point of the resultant compound of Compound exemplifying number [20] is unclear. The infrared absorption spectrum of the compound of Compound exemplifying number [20] is shown in FIG. 7, and the $^1$H NMR spectrum thereof ($^1$H-NMR, solvent: CDCl$_3$, the same being applied correspondingly to any NMR spectrum in the following) is shown in FIG. 8.

The glass transition temperature of the compound of Compound exemplifying number [20] is 63.9° C., the ionization potential thereof is 5.39 eV, and the charge mobility thereof is 2.45×10$^{-7}$ cm$^2$/Vs.

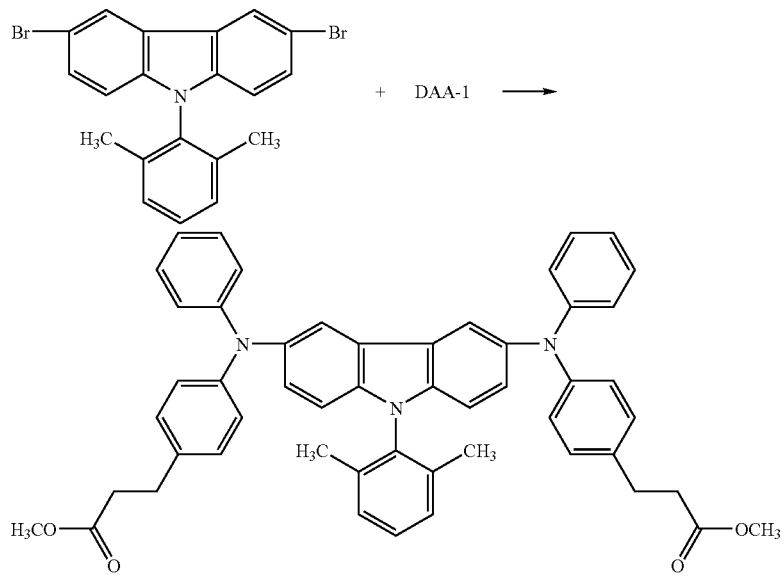

Example 5

Into a 50 mL three-necked eggplant shaped flask are put 1.5 g of a compound of Compound exemplifying number [14], 10 mL of ethylene glycol, and 0.02 g of tetrabutoxytitanium, and then the solution is heated and stirred at 200° C. for 5 hours under the atmosphere of nitrogen.

It is ascertained by TLC that the raw material 1 disappears. Subsequently, the pressure is reduced to 50 Pa to distill off ethylene glycol while the solution is heated to 210° C. to continue the reaction for 6 hours. Thereafter, the system is cooled to room temperature, and the resultant is dissolved in 50 mL of tetrahydrofuran. Insoluble matters are filtrated off with a 0.5 μL polytetrafluoroethylene (PTFE) filter. The filtrate is distilled under a reduced pressure, and then the residue is dissolved into 300 mL of monochlorobenzene. The resultant is washed with 300 mL of 1 N HCl one time and 500 mL of water three times successively.

The monochlorobenzene solution is distilled to 30 mL under a reduced pressure, and the residue is added dropwise to 800 mL of a mixed solvent of ethyl acetate and methanol (=1/3) to reprecipitate a polymer. The resultant polymer is collected by filtration, and then sufficiently washed with methanol. Thereafter, the resultant is subjected to vacuum drying at 60° C. for 16 hours to yield 0.9 g of a polymer (Polymer exemplifying number (10) in <List (2)>). The molecular weight of this polymer is measured with a device for gel permeation chromatography (GPC) (trade name: HLC-8120 GPC, manufactured by Tosoh Corp.). As a result, the weight-average molecular weight Mw is $6.1 \times 10^4$ (in terms of styrene). The molecule distribution Mw/Mn is 2.12, and the polymerization degree p calculated from the molecular weight of the monomer is 76.

Figure 9:
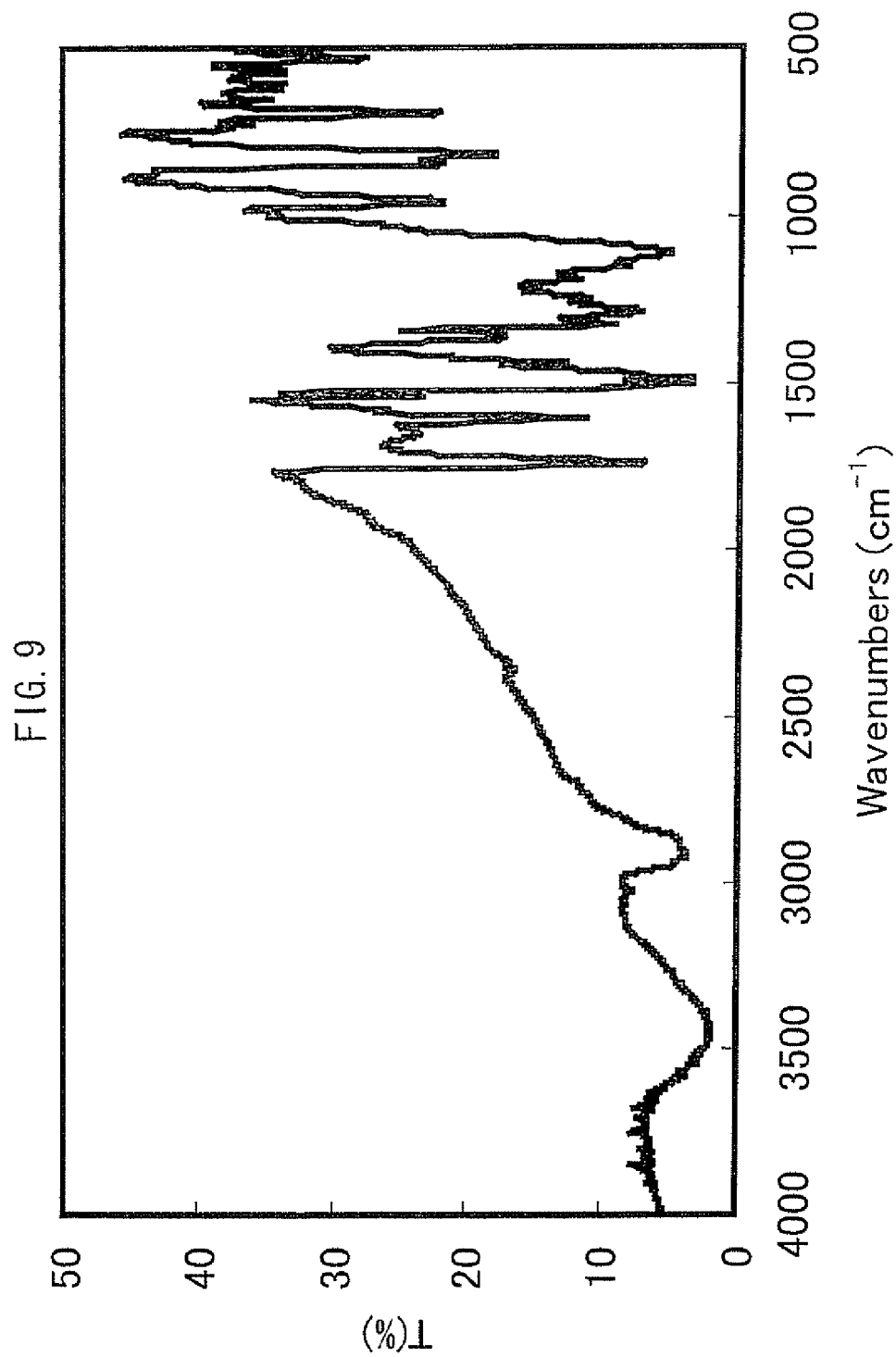
FIG. 9 is an IR spectrum of a compound obtained in Example 5.
Figure 10:
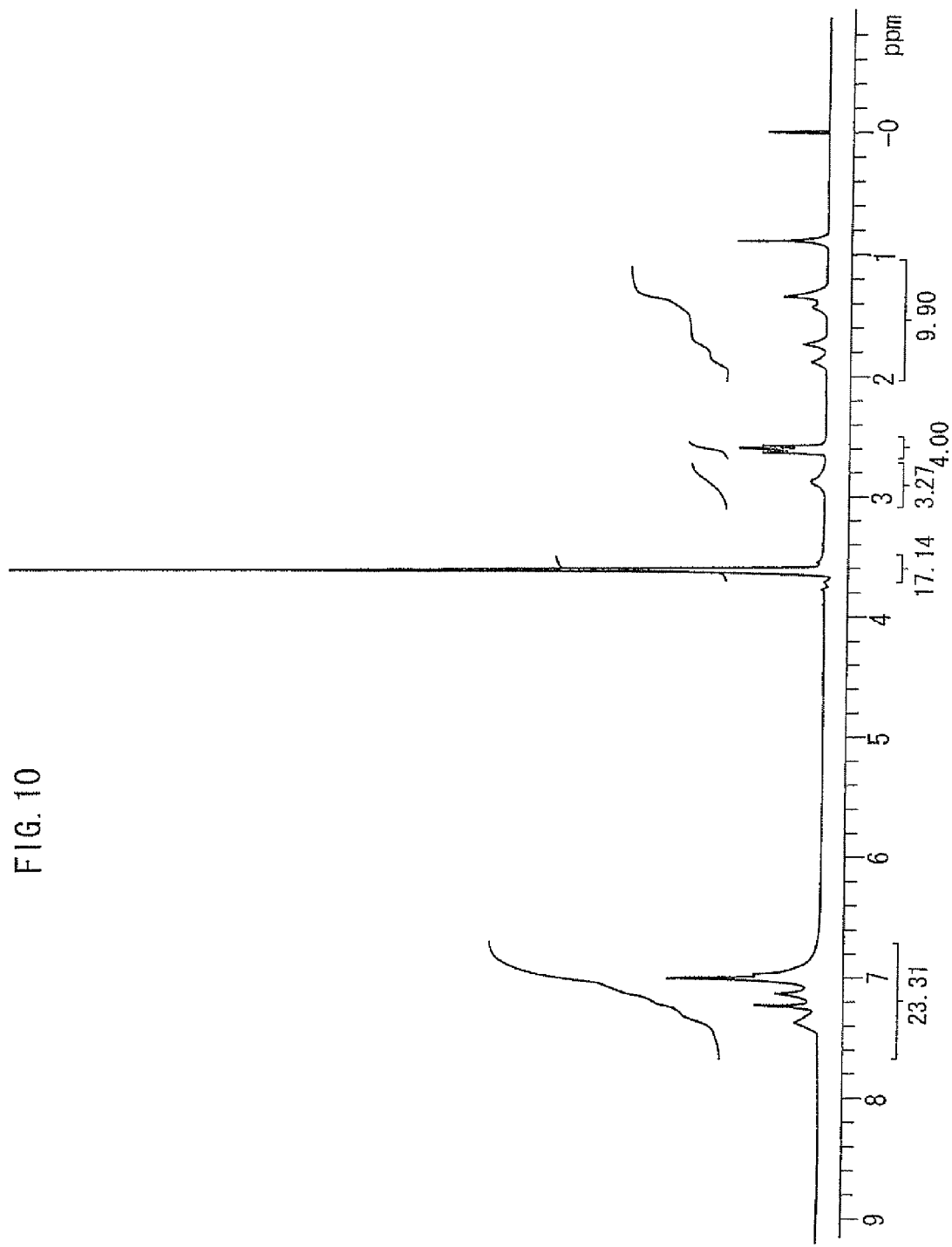
FIG. 10 is a $^1$H-NMR spectrum of the compound obtained in Example 5.

The infrared absorption spectrum of the resultant polymer of Polymer exemplifying number (10) is shown in FIG. 9, and the $^1$H NMR spectrum thereof ($^1$H-NMR, solvent: CDCl$_3$, the same rule being applied correspondingly to any NMR spectrum in the following) is shown in FIG. 10.

The glass transition temperature of the polymer of Polymer exemplifying number (10) is 101.2° C., the ionization potential thereof is 5.43 eV, and the charge mobility thereof is $9.32 \times 10$ cm$^2$/Vs.

In the examples, each of the charge mobilities is measured with a device for the time-of-flight method (trade name: TOF-401, manufactured by Optel Co., Ltd.). Each of the melting points and glass transition temperatures is measured with a meter for differential scanning calorimetry (DSC) (trade name: Tg/DTA 6200, manufactured by Seiko Instruments Ltd.). The charge mobility measurement about each of the low molecular weight compounds is made by using a film wherein 40% by mass of the compound is dispersed in polycarbonate (20% by mass of the compound is dispersed therein only in Example 2) unless otherwise specified.

What is claimed is:

1. A carbazole compound represented by the following formula (I):

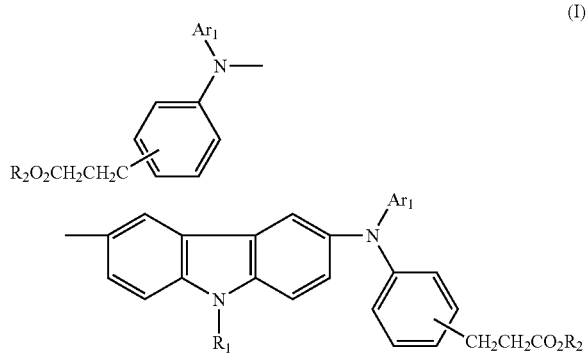

(I)

wherein each Ar$_1$ independently represents a substituted or unsubstituted monovalent aromatic group or an aromatic group containing a heteroring, and R$_1$ and each R$_2$ independently represents a hydrogen atom, an alkyl group, a substituted or unsubstituted aryl group, or a substituted or unsubstituted aralkyl group.

2. A carbazole compound polymer represented by the following formula (II):

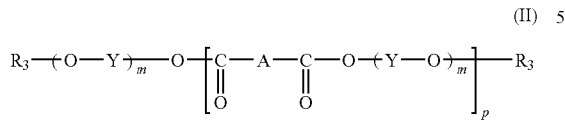

(II)

wherein each Y independently represents a bivalent hydrocarbon group, each $R_3$ independently represents a hydrogen atom, an alkyl group, a substituted or unsubstituted aryl group, or a substituted or unsubstituted aralkyl group, each m independently represents an integer of from 1 to 5, p represents an integer of from 5 to 5,000, and A represents a group represented by the following formula (III):

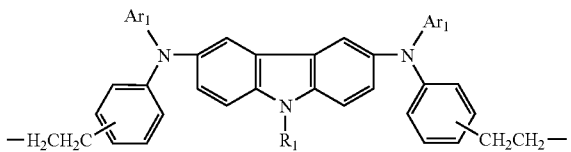

(III)

wherein each $Ar_1$ independently represents a substituted or unsubstituted monovalent aromatic group or an aromatic group containing a heteroring, and $R_1$ represents a hydrogen atom, an alkyl group, a substituted or unsubstituted aryl group, or a substituted or unsubstituted aralkyl group.

* * * * *